US010377792B2

(12) United States Patent
Fernando et al.

(10) Patent No.: US 10,377,792 B2
(45) Date of Patent: Aug. 13, 2019

(54) MOISTURE DISPLACEMENT AND SIMULTANEOUS MIGRATION OF SURFACE-FUNCTIONALIZED ALGAE FROM WATER TO AN EXTRACTION SOLVENT USING IONIC POLYELECTROLYTES

(71) Applicant: The Texas A&M University System, College Station, TX (US)

(72) Inventors: Sandun D. Fernando, College Station, TX (US); Varun M. Gejji, Pune (IN)

(73) Assignee: The Texas A&M University System, College Station, TX (US)

( * ) Notice: Subject to any disclaimer, the term of this patent is extended or adjusted under 35 U.S.C. 154(b) by 185 days.

(21) Appl. No.: 15/457,650

(22) Filed: Mar. 13, 2017

(65) Prior Publication Data

US 2017/0267715 A1    Sep. 21, 2017

Related U.S. Application Data

(60) Provisional application No. 62/309,293, filed on Mar. 16, 2016.

(51) Int. Cl.
*C07K 1/14* (2006.01)
*C07K 14/40* (2006.01)
(Continued)

(52) U.S. Cl.
CPC .............. *C07K 1/145* (2013.01); *B01D 11/02* (2013.01); *B01J 39/20* (2013.01); *B01J 41/14* (2013.01);
(Continued)

(58) Field of Classification Search
CPC ........ C07K 1/145; C07K 14/405; C07K 1/14; C12P 7/64; C11B 1/10; C11B 1/108; C11B 1/04; C11B 1/12; C11B 3/00; C11B 3/001; C11B 3/006; C11B 3/02; C11B 3/04; C11B 11/02; C11B 11/0203; B01J 43/00; B01J 39/20; B01J 41/14; B01D 11/02; B01D 11/0207; B01D 11/0288; C02F 1/26;
(Continued)

(56) References Cited

U.S. PATENT DOCUMENTS 5,591,772 A *   1/1997  Lane .................... A61K 31/05
                                                        514/458
6,166,231 A    12/2000  Hoeksema ...................... 554/12
(Continued)

OTHER PUBLICATIONS

Akardere, E. et al. (2010) "Three-phase partitioning of invertase from Baker's yeast," *Separation and Purification Technology* 72(3), 335-339.
(Continued)

*Primary Examiner* — Joseph W Drodge
(74) *Attorney, Agent, or Firm* — Medlen & Carroll, LLP

(57) ABSTRACT

This invention is in the field of micro-organism and algal cell processing. The invention relates to a method of maximizing migration of micro-organism and/or algal cells to a solvent fraction while simultaneously displacing water in a separate fraction and subsequent extraction of hydrophobic products from the organisms. The invention further relates to a method of sequestration of protein from an aqueous phase to an organic solvent.

11 Claims, 26 Drawing Sheets

(51) Int. Cl.
  *B01J 41/14*  (2006.01)
  *B01J 39/20*  (2006.01)
  *C11B 1/10*  (2006.01)
  *C12P 7/64*  (2006.01)
  *B01D 11/02*  (2006.01)
  *C07K 14/405*  (2006.01)
  *B01J 43/00*  (2006.01)

(52) U.S. Cl.
  CPC ............. *B01J 43/00* (2013.01); *C07K 14/405* (2013.01); *C11B 1/10* (2013.01); *C11B 1/108* (2013.01); *C12P 7/64* (2013.01)

(58) Field of Classification Search
  CPC .... C02F 2103/22; C02F 2103/26; A23K 1/14; A23K 1/288; C10L 1/02; C10L 1/10; C10L 1/026; C10L 1/1802; C10L 1018/08; C10L 1015/42; C10L 2200/0476; C10L 2200/0484; Y02E 50/10; Y02E 50/13; Y02E 10/34; C11C 3/00; C11C 3/02; C11C 3/003
  USPC ...... 210/167.21, 170.02, 170.11, 257.1, 511, 210/634; 44/307, 385, 605; 47/1.4, 60, 47/62, 62 R, 62 A; 554/8, 174, 175; 119/213, 215, 226; 530/370, 412, 422
  See application file for complete search history.

(56) References Cited

U.S. PATENT DOCUMENTS

| | | | |
|---|---|---|---|
| 7,431,952 B2 | 10/2008 | Bijl et al. ...................... | 424/780 |
| 7,749,392 B2 | 7/2010 | Whittaker et al. ............ | 210/727 |
| 2006/0214104 A1* | 9/2006 | Pope .................. | G01N 33/6851 250/297 |
| 2008/0052987 A1* | 3/2008 | Busch ................... | A01G 31/06 47/62 R |
| 2010/0068772 A1 | 3/2010 | Downey ....................... | 435/134 |
| 2010/0261922 A1 | 10/2010 | Fleischer et al. ............. | 554/206 |
| 2010/0304452 A1 | 12/2010 | Oyler ........................... | 435/134 |
| 2011/0192793 A1* | 8/2011 | Chew ........................ | C12N 1/06 210/633 |
| 2011/0293785 A1* | 12/2011 | Franklin ................... | A23D 7/00 426/61 |
| 2012/0145643 A1* | 6/2012 | Pandya ..................... | C02F 1/56 210/705 |
| 2012/0184759 A1* | 7/2012 | Kipp ...................... | B01D 63/02 554/175 |
| 2012/0264194 A1* | 10/2012 | Kale ......................... | C11B 1/10 435/257.1 |
| 2013/0072701 A1* | 3/2013 | Chew ......................... | C11B 1/10 554/8 |
| 2013/0211113 A1* | 8/2013 | Eckelberry ............. | C11B 3/005 554/1 |
| 2015/0351389 A1* | 12/2015 | Kolari ..................... | A01N 37/34 210/764 |

OTHER PUBLICATIONS

Asenjo, J. A. et al. (2011) "Aqueous two-phase systems for protein separation: a perspective," *Journal of Chromatography A* 1218(49), 8826-8835.
Asenjo, J. A. et al. (2012) "Aqueous two-phase systems for protein separation: phase separation and applications," *Journal of Chromatography A* 1238, 1-10.
Becker, E. W. (2007) "Micro-algae as a source of protein," *Biotechnology Advances* 25(2), 207-210.
Brennan, L. et al. (2010) "Biofuels from microalgae—a review of technologies for production, processing, and extractions of biofuels and co-products," *Renewable and Sustainable Energy Reviews* 14(2), 557-577.
Brune, D. E. et al. (2008) Algal production and harvest for food, feed, and biofuels, in *2008 Microalgae Biomass Summit*, Algal Biomass Organization, Seattle, Wash.
Buckwalter, P. et al. (2013) "Dewatering microalgae by forward osmosis," *Desalination* 312, 19-22.
Buelna, G. et al. (1990) "Evaluation of various flocculants for the recovery of algal biomass grown on pig-waste," *Biological Wastes* 31(3), 211-222.
Chen, C.-Y. et al. (2011) "Cultivation, photobioreactor design and harvesting of microalgae for biodiesel production: A critical review," *Bioresource Technology* 102(1), 71-81.
Chisti, Y. (2007) "Biodiesel from microalgae," *Biotechnology Advances* 25(3), 294-306.
Chiu, S.-Y. et al. (2009) "Lipid accumulation and CO2 utilization of Nannochloropsis oculata in response to CO2 aeration," *Bioresource Technology* 100(2), 833-838.
Cooney, M. (2013) "Case Studies of Separation in Biorefineries—Extraction of Algae Oil from Microalgae," *Separation and Purification Technologies in Biorefineries*, 533-554.
Coward, T. et al. (2013) "Development of a foam flotation system for harvesting microalgae biomass," *Algal Research* 2(2), 135-144.
Davis, R. et al. (2011) "Techno-economic analysis of autotrophic microalgae for fuel production," *Applied Energy* 88(10), 3524-3531.
Dejoye Tanzi, C. et al. (2013) "New procedure for extraction of algal lipids from wet biomass: A green clean and scalable process," *Bioresource Technology* 134, 271-275.
Delrue, F. et al. (2012) "An economic, sustainability, and energetic model of biodiesel production from microalgae," *Bioresource Technology* 111, 191-200.
Demirbas, A. (2010) "Use of algae as biofuel sources," *Energy Conversion and Management* 51(12), 2738-2749.
Dennison, C. et al. (1997) "Three phase partitioning: concentration and purification of proteins," *Protein Expression and Purification* 11(2), 149-161.
Divakaran, R. et al. (2002) "Flocculation of algae using chitosan," *Journal of Applied Phycology* 14(5), 419-422.
Dogan, N. et al. (2008) "Characterization of three-phase partitioned exo-polygalacturonase from Aspergillus sojae with unique properties," *Biochemical Engineering Journal* 39(1), 43-50.
Ehimen, E. A. et al. (2010) "Variables affecting the in situ transesterification of microalgae lipids," *Fuel* 89(3), 677-684.
Fairhurst, D. (2013) "An Overview of the Zeta Potential Part 3: Uses and Applications," *American Pharmaceutical Review*.
Golueke, C. G. et al. (1965) "Harvesting and processing sewage-grown planktonic algae," *Journal of the Water Pollution Control Federation* 37(4), 471-498.
Gouveia, L. (2011) "Microalgae as a feedstock for biofuels," in *Microalgae as a Feedstock for Biofuels*, pp. 1-69, Springer.
Griffiths, M. J. et al. (2010) "Selection of direct transesterification as the preferred method for assay of fatty acid content of microalgae," *Lipids* 45(11), 1053-1060.
Grima, E. M. et al. (2003) "Recovery of microalgal biomass and metabolites: process options and economics," *Biotechnology Advances* 20(7), 491-515.
Harith, Z. T. Y., F. M. et al. (2009) "Effect of different flocculants on the flocculation performance of microalgae, chaetoceros calcitrans, cells," *African Journal of Biotechnology* 8(21), 5971-5978.
Harun, R. et al. (2010) "Bioprocess engineering of microalgae to produce a variety of consumer products," *Renewable and Sustainable Energy Reviews* 14, 1037-1047.
Henderson, R. K. et al. (2010) "The impact of differing cell and algogenic organic matter (AOM) characteristics on the coagulation and flotation of algae," *Water Research* 44(12), 3617-3624.
Kanda, H. et al. (2011) "Simple extraction method of green crude from natural blue-green microalgae by dimethyl ether," *Fuel* 90(3), 1264-1266.
Klitzing, R. v. et al. (2002) "Structuring of poly(DADMAC) chains in aqueous media: a comparison between bulk and free-standing film measurements," *Physical Chemistry Chemical Physics* 4(10), 1907-1914.

(56) References Cited

OTHER PUBLICATIONS

Lardon, L. et al. (2009) "Life-Cycle Assessment of Biodiesel Production from Microalgae," *Environmental Science & Technology* 43(17), 6475-6481.

Li, Q. et al. (2008) "Perspectives of microbial oils for biodiesel production," *Applied Microbiology and Biotechnology* 80(5), 749-756.

Marcozzi, G. et al. (1998) "Effects of surfactants on the stabilization of the bovine lactoperoxidase activity," *Biotechnology Progress* 14(4), 653-656.

Molina, E. et al. (2001) "Tubular photobioreactor design for algal cultures," *Journal of Biotechnology* 92(2), 113-131.

Molina Grima, E. et al. (2003) "Recovery of microalgal biomass and metabolites: process options and economics," *Biotechnology Advances* 20(7-8), 491-515.

Mondal, K. et al. (2006) "Emerging options in protein bioseparation," in *Biotechnology Annual Review* (El-Gewely, M. R., Ed.), pp. 1-29, Elsevier.

Moriyama, Y. et al. (2005) "Protective effects of small amounts of bis (2-ethylhexyl) sulfosuccinate on the helical structures of human and bovine serum albumins in their thermal denaturations," *Langmuir* 21(12), 5524-5528.

O'Connell, D. et al. (2012) "Life cycle assessment of dewatering routes for algae derived biodiesel processes," *Clean Technologies and Environmental Policy*, 1-11.

Pei, Y. et al. (2009) "Ionic liquid-based aqueous two-phase extraction of selected proteins," *Separation and Purification Technology* 64(3), 288-295.

Pragya, N. et al. (2013) "A review on harvesting, oil extraction and biofuels production technologies from microalgae," *Renewable and Sustainable Energy Reviews* 24, 159-171.

Richard, T. L. (2010) "Challenges in scaling up biofuels infrastructure," *Science* 329(5993), 793-796.

Salamanca, M. H. et al. (1998) "On the kinetics of phase separation in aqueous two-phase systems," *Journal of Chromatography B: Biomedical Sciences and Applications* 711(1), 319-329.

Samarasinghe, N. et al. (2012) "Effect of high pressure homogenization on aqueous phase solvent extraction of lipids from nannochloris oculata microalgae," *Journal of Energy and Natural Resources* 1(1), 7.

Samarasinghe, N. et al. (2012) "Algal cell rupture using high pressure homogenization as a prelude to oil extraction," *Renewable Energy* 48, 300-308.

Sheehan, J. et al. (1998) A look back at the US Department of Energy's aquatic species program—Biodiesel from algae (NREL/TP-580-24190), (National Renewable Energy Laboratog (NREL), Ed.), US DOE, Golden, CO.

Microalgae harvesting and processing: a literature review dated.

Sim, T. et al. (1988) "Comparison of centrifugation, dissolved air flotation and drum filtration techniques for harvesting sewage-grown algae," *Biomass* 16, 51-62.

Spolaore, P. et al. (2006) "Commercial applications of microalgae," *Journal of Bioscience and Bioengineering* 101(2), 87-96.

U.S. Doe. (2010) National Algal Biofuels Technology Roadmap, (Energy, U. S. D. o., Ed.), Office of Energy Efficiency and Renewable Energy, Biomass Program.

Uduman, N. et al. (2010) "Dewatering of microalgal cultures: a major bottleneck to algae-based fuels," *Journal of renewable and sustainable energy* 2(1), 012701.

Wati, R. K. et al. (2009) "Three-phase partitioning of trypsin inhibitor from legume seeds," *Process Biochemistry* 44(12), 1307-1314.

Wijffels, R. H. et al. (2010) "Microalgae for the production of bulk chemicals and biofuels," *Biofuels, Bioproducts and Biorefining* 4(3), 287-295.

Yuan, W. et al. (2009) "Microalgae mass production methods," *Transactions of the ASABE* 52(4), 1275-1287.

Zittelli, G. C. et al. (1999) "Production of eicosapentaenoic acid by *Nannochloropsis* sp. cultures in outdoor tubular photobioreactors," *Journal of Biotechnology* 70, 299-312.

\* cited by examiner

FIG.3A                                FIG.3B

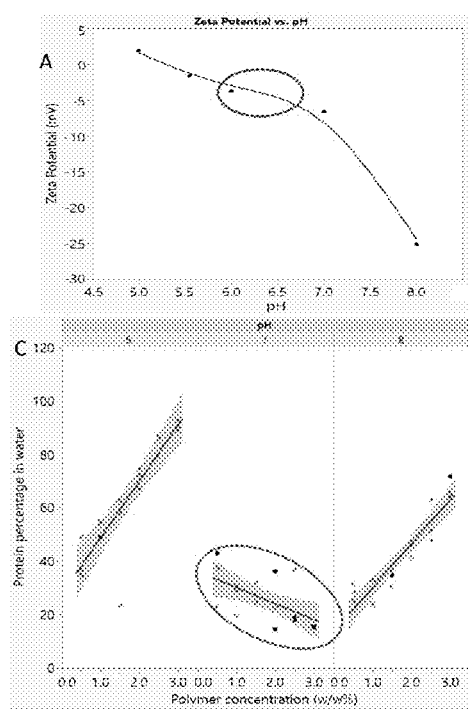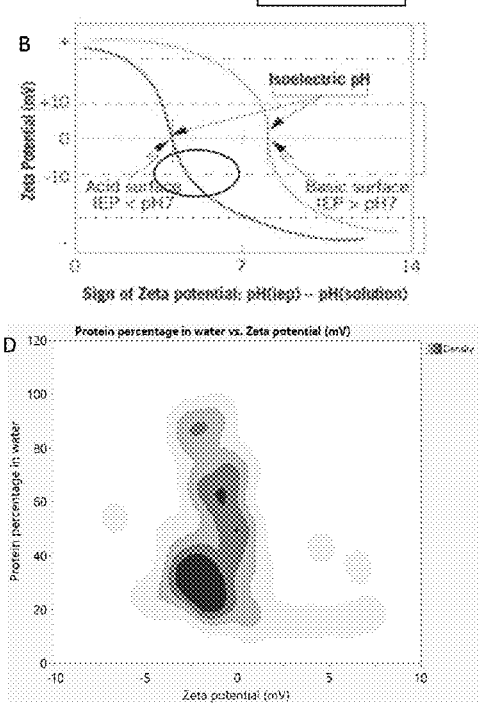
FIGURE 25A – 25D

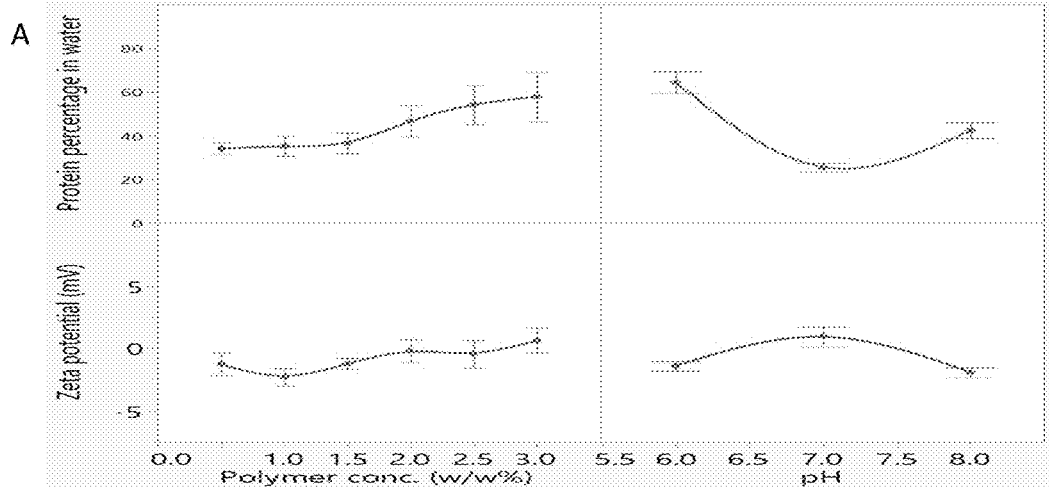
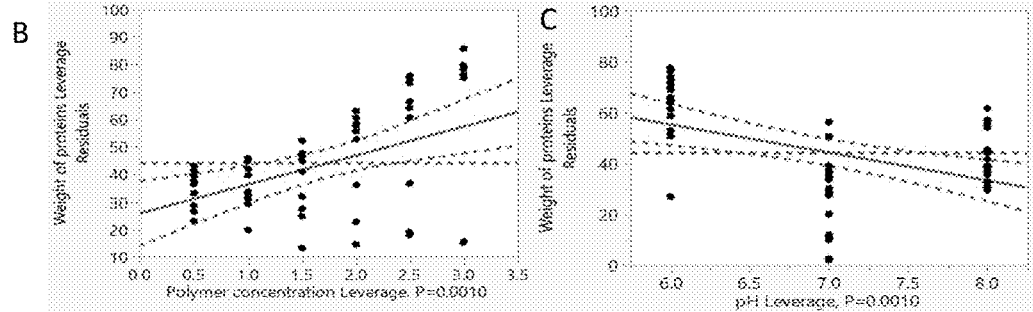
FIGURE 26A – 26C

10,377,792 B2

MOISTURE DISPLACEMENT AND SIMULTANEOUS MIGRATION OF SURFACE-FUNCTIONALIZED ALGAE FROM WATER TO AN EXTRACTION SOLVENT USING IONIC POLYELECTROLYTES

CROSS-REFERENCE TO RELATED APPLICATIONS

The present application claims the benefit of U.S. Provisional Patent Application No. 62/309,293, filed on Mar. 16, 2016, which is incorporated herein by reference.

STATEMENT OF GOVERNMENTAL SUPPORT

This invention was made with government support awarded by the United States Department of Energy (US-DOE) through National. Alliance for Advanced Biofuels and Bioproducts (NAABB) (Grant NumberDE-EE0003046). The government has certain rights in the invention.

FIELD OF THE INVENTION

This invention is in the field of micro-organism and algal cell processing. The invention relates to a method of maximizing migration of micro-organism and/or algal cells to a solvent fraction while simultaneously displacing water in a separate fraction and subsequent extraction of hydrophobic products from the organisms. The invention further relates to a method of sequestration of protein from an aqueous multi-component suspension to an extracting solvent.

BACKGROUND OF THE INVENTION

Efficient microalgae dewatering is a major problem that continuously plagues industrial-scale processing of microalgae metabolites for commercial use. Large scale cultivation of algal biomass is typically produced with a high volume of water, in some cases greater than 95%. As a result, harvesting concentrated microalgal cultures presents a significant economic challenge to industries such as algae-based fuels that are critically dependent on improvement of techniques and practices designed to remove algae from water. What is needed is a technique designed to maximize migration of algal cells to a solvent fraction while simultaneously displacing water in a separate fraction.

SUMMARY OF THE INVENTION

This invention is in the field of micro-organism and algal cell processing. The invention relates to a method of maximizing migration of micro-organism and/or algal cells to a solvent fraction while simultaneously displacing water in a separate fraction and subsequent extraction of hydrophobic products from the organisms. The invention further relates to a method of sequestration of protein from an aqueous multi-component suspension to an extracting solvent. In some embodiments, the process displaces extracellular as well as internal (intracellular) water.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In one embodiment, the invention contemplates a method for the extraction of algal oil comprising: a) providing: i) algae cells comprising algal oil and a hydrophilic cell surface; ii) an amphiphilic agent capable of converting said hydrophilic cell surface to a hydrophobic cell surface; and iii) an extractant; b) adding said amphiphilic agent to said algae cells under conditions such that said hydrophobic cell surface is created, and c) purifying said algal oil with said extractant. In one embodiment, said algae cells comprise an aqueous solution/phase. In one embodiment, said algae cells are in an aqueous solution/phase. In one embodiment, said amphiphilic agent is Poly(diallyldimethylammonium chloride). In one embodiment, said amphiphilic agent is Poly (sodium 4-styrenesulfonate). In one embodiment, said amphiphilic agent is Poly(3-(1-Pyridinio)-1-propanesulfonate). In one embodiment, said amphiphilic agent is a monomeric form of at least one of the group consisting of diallyldimethylammonium chloride, sodium 4-styrenesulfonate, and 3-(1-Pyridinio)-1-propanesulfonate. In one embodiment, said amphiphilic agent is an oligomeric form of at least one of the group consisting of diallyldimethylammonium chloride, sodium 4-styrenesulfonate, and 3-(1-Pyridinio)-1-propanesulfonate. In one embodiment, said purifying releases said algal oil from said algae cells. In one embodiment, said purifying comprises using a homogenizer to release said algal oil from said algae cells. In one embodiment, said method further comprises purifying said released algal oil with said extractant. In one embodiment, said algae cells are *Nannochloropsis oculata*. In one embodiment, said algae cells are *Chlorella vulgaris*. In one embodiment, said extractant comprises non-polar solvent. In one embodiment, said extractant comprises a water-immiscible solvent. In one embodiment, said water-immiscible solvent comprises hexane. In one embodiment, said method further comprises vigorously mixing polymeric/oligomeric/monomeric cationic electrolytes and hydrophobic ligands/residues (such as poly/monomeric diallyl dimethyl ammonium chloride (DADMAC)) to said algae cells in a water solution. In one embodiment, said method further comprises mixing a water-immiscible solvent to said water solution to produce a biphasic mixture. In one embodiment, said method further comprises separating the biphasic mixture. In one embodiment, the separating comprises allowing the mixture to stand undisturbed. In one embodiment, the separating further comprises concentrating the electrolyte-bound algae in the water-immiscible solvent phase. In one embodiment, the method further comprises isolating the aqueous phase from the water-immiscible solvent phase. In one embodiment, the isolating comprises use of a device including, but not limited to, a micropipette, syringe or a separatory funnel. In one embodiment, the method further comprises performing a gravimetric analysis on the aqueous phase or the water immiscible solvent phase. In one embodiment, said method further comprises diluting said cationic electrolyte polymers in water. In one embodiment, the diluted cationic electrolyte polymers are added to an algal suspension. Although it is not necessary to understand the mechanism of an invention it is believed that diluted polymers ensure polymer dispersion to improve surface coverage of the polymer on the algae suspension. In one embodiment, the method further comprises modulating hydrophobicity of the polymer-coated algae surface. In one embodiment, the polymer-coated algae surface hydrophobicity is modulated by changing at least one electrolyte hydrophobic ligand/residue. In one embodiment, the electrolyte forms fissures in the algal surface promoting internal water removal. In one embodiment, the method further comprises purifying said algae from a biological matrix. In one embodiment, the purifying comprises using anionic or cationic electrolytes. In one embodiment, said algal oil (lipids) is directly absorbed to extractant (e.g. hexane) phase. In one embodiment, said algae cells comprise algal protein and a hydrophilic cell surface. In one embodiment, said proteins are manipulated, depending on pH of said aqueous phase, to be moved to extractant (e.g. hexane) or retained in aqueous phase. In one embodiment, modulating the pH of the aqueous phase, various components (oil or protein) are manipulated to migrate into the extractant or said aqueous phase.

In one embodiment, the invention contemplates a method for the extraction of algal protein, comprising: a) providing: i) an aqueous solution containing algae cells, said algae cells comprising hydrophilic algal protein; ii) an amphiphilic agent capable of converting said hydrophilic algal protein to a hydrophobic algal protein; and iii) an extractant; b) adding said amphiphilic agent to said algae cells under conditions such that said hydrophobic algal protein is created, and c) purifying said algal protein with said extractant. In one embodiment, said amphiphilic agent is Poly(diallyldimethylammonium chloride). In one embodiment, said amphiphilic agent is Poly(sodium 4-styrenesulfonate). In one embodiment, wherein said amphiphilic agent is Poly(3-(1-Pyridinio)-1-propanesulfonate). In one embodiment, said amphiphilic agent is a monomeric form of at least one of the group consisting of diallyldimethylammonium chloride, sodium 4-styrenesulfonate, and 3-(1-Pyridinio)-1-propanesulfonate. In one embodiment, said amphiphilic agent is an oligomeric form of at least one of the group consisting of diallyldimethylammonium chloride, sodium 4-styrenesulfonate, and 3-(1-Pyridinio)-1-propanesulfonate. In one embodiment, the purifying releases said algal protein from said algae cells. In one embodiment, said purifying uses a homogenizer to release said algal protein from said algae cells. In one embodiment, said method further comprises purifying said released algal protein with said extractant. In one embodiment, said algae cells are *Nannochloropsis oculata*. In one embodiment, said algae cells are *Chlorella vulgaris*. In one embodiment, said extractant comprises non-polar solvent. In one embodiment, said extractant comprises hexane. In one embodiment, said the ratio of extractant to aqueous solution is 2:1 or less. In one embodiment, said proteins are manipulated, depending on pH of said aqueous solution, to be moved to extractant (e.g. hexane) or retained in aqueous phase. In one embodiment, modulating the pH of the aqueous solution, various components (oil or protein) are manipulated to migrate into the extractant or said aqueous solution.

In one embodiment, the invention contemplates a method for the extraction of protein, comprising: a) providing: i) an aqueous solution containing a complex multi-component suspension, said complex multi-component suspension comprising hydrophilic protein; ii) an amphiphilic agent capable of converting said hydrophilic protein to a hydrophobic protein; and iii) an extractant; b) adding said amphiphilic agent to said complex multi-component suspension under conditions such that said hydrophobic protein is created, and c) purifying said protein with said extractant. In one embodiment, said amphiphilic agent is Poly(diallyldimethylammonium chloride). In one embodiment, said amphiphilic agent is Poly(sodium 4-styrenesulfonate). In one embodiment, wherein said amphiphilic agent is Poly(3-(1-Pyridinio)-1-propanesulfonate). In one embodiment, said amphiphilic agent is a monomeric form of at least one of the group consisting of diallyldimethylammonium chloride, sodium 4-styrenesulfonate, and 3-(1-Pyridinio)-1-propanesulfonate. In one embodiment, said amphiphilic agent is an oligomeric form of at least one of the group consisting of diallyldimethylammonium chloride, sodium 4-styrenesulfonate, and 3-(1-Pyridinio)-1-propanesulfonate. In one embodiment, said complex multi-component suspension comprises broken down cells. In one embodiment, said complex multi-component suspension comprises major cellular components (such as carbohydrates, lipids and other cellular debris). In one embodiment, the purifying releases said protein from said complex multi-component suspension. In one embodiment, said purifying uses a homogenizer to release said protein from said complex multi-component suspension. In one embodiment, said method further comprises purifying said released protein with said extractant. In one embodiment, said complex multi-component suspension comprises non-algal proteins. In one embodiment, said complex multi-component suspension comprises microorganisms. In one embodiment, said extractant comprises non-polar solvent. In one embodiment, said extractant comprises hexane. In one embodiment, said the ratio of extractant to aqueous solution is 2:1 or less. In one embodiment, said proteins are manipulated, depending on pH of said aqueous solution, to be moved to extractant (e.g. hexane) or retained in aqueous phase. In one embodiment, modulating the pH of the aqueous solution, various components (oil or protein) are manipulated to migrate into the extractant or said aqueous solution.

In one embodiment, the invention contemplates a method for the extraction of protein, comprising: a) providing: i) an aqueous solution containing a multi-component suspension, said multi-component suspension comprising hydrophilic protein; ii) an amphiphilic agent capable of converting said hydrophilic protein to a hydrophobic protein; and iii) an extractant; b) adding said amphiphilic agent to said multi-component suspension, and c) purifying said protein with said extractant. In one embodiment, said amphiphilic agent is Poly(diallyldimethylammonium chloride). In one embodiment, said amphiphilic agent is Poly(sodium 4-styrenesulfonate). In one embodiment, wherein said amphiphilic agent is Poly(3-(1-Pyridinio)-1-propanesulfonate). In one embodiment, said amphiphilic agent is a monomeric form of at least one of the group consisting of diallyldimethylammonium chloride, sodium 4-styrenesulfonate, and 3-(1-Pyridinio)-1-propanesulfonate. In one embodiment, said amphiphilic agent is an oligomeric form of at least one of the group consisting of diallyldimethylammonium chloride, sodium 4-styrenesulfonate, and 3-(1-Pyridinio)-1-propanesulfonate. In one embodiment, said multi-component suspension comprises broken down cells. In one embodiment, said multi-component suspension comprises major cellular components (such as carbohydrates, lipids and other cellular debris). In one embodiment, the purifying releases said protein from said multi-component suspension. In one embodiment, said purifying uses a homogenizer to release said protein from said multi-component suspension. In one embodiment, said method further comprises purifying said released protein with said extractant. In one embodiment, said multi-component suspension comprises non-algal proteins. In one embodiment, said multi-component suspension comprises microorganisms. In one embodiment, said extractant comprises non-polar solvent. In one embodiment, said extractant comprises hexane. In one embodiment, said the ratio of extractant to aqueous solution is 2:1 or less. In one embodiment, said proteins are manipulated, depending on pH of said aqueous solution, to be moved to extractant (e.g. hexane) or retained in aqueous phase. In one embodiment, modulating the pH of the aqueous solution, various components (oil or protein) are manipulated to migrate into the extractant or said aqueous solution.

In one embodiment, the invention contemplates a method for the extraction of protein, comprising: a) providing: i) an aqueous solution containing a multi-component suspension, said multi-component suspension comprising hydrophilic protein; ii) an amphiphilic agent; and iii) an extractant; b) adding said amphiphilic agent to said multi-component suspension, and c) purifying said protein with said extractant. In one embodiment, said amphiphilic agent associates with said hydrophilic protein under such conditions that said protein attains hydrophobic properties. In one embodiment, said amphiphilic agent is Poly(diallyldimethylammonium chloride). In one embodiment, said amphiphilic agent is Poly(sodium 4-styrenesulfonate). In one embodiment, wherein said amphiphilic agent is Poly(3-(1-Pyridinio)-1-propanesulfonate). In one embodiment, said amphiphilic agent is a monomeric form of at least one of the group consisting of diallyldimethylammonium chloride, sodium 4-styrenesulfonate, and 3-(1-Pyridinio)-1-propanesulfonate. In one embodiment, said amphiphilic agent is an oligomeric form of at least one of the group consisting of diallyldimethylammonium chloride, sodium 4-styrenesulfonate, and 3-(1-Pyridinio)-1-propanesulfonate. In one embodiment, said multi-component suspension comprises broken down cells. In one embodiment, said multi-component suspension comprises major cellular components (such as carbohydrates, lipids and other cellular debris). In one embodiment, the purifying releases said protein from said multi-component suspension. In one embodiment, said purifying uses a homogenizer to release said protein from said multi-component suspension. In one embodiment, said method further comprises purifying said released protein with said extractant. In one embodiment, said multi-component suspension comprises non-algal proteins. In one embodiment, said multi-component suspension comprises microorganisms. In one embodiment, said extractant comprises non-polar solvent. In one embodiment, said extractant comprises hexane. In one embodiment, said the ratio of extractant to aqueous solution is 2:1 or less. In one embodiment, said proteins are manipulated, depending on pH of said aqueous solution, to be moved to extractant (e.g. hexane) or retained in aqueous phase. In one embodiment, modulating the pH of the aqueous solution, various components (oil or protein) are manipulated to migrate into the extractant or said aqueous solution.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The use of the word "a" or "an" when used in conjunction with the term "comprising" is used herein to describe "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

The terms "inhibiting" or "reducing" or any variation of these terms, when is used herein to describe any measurable decrease or complete inhibition to achieve a desired result.

The term "effective," as that term is used herein to describe adequate to accomplish a desired, expected, or intended result.

As used herein, the term "algae" or "algae cells" is used herein to describe various algal species. Algal sources can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis* chuff, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Cryptheco-dinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleuracatpsa, Prochlorococcus, Prochloron, Prochlorothrix, Pseudanabaena, Rivularia, Schizothrix, Scytonema, Spirulina, Stanieria, Starria, Stigonema, Symploca, Syn-*

*echococcus, Synechocystis, Tolypothrix, Trichodesmium, Tychonema*, and *Xenococcus* species.

As used herein, the tell "harvesting" is used herein to describe the concentration of algal cells by various methods including, but not limited to coagulation, flocculation, flotation, centrifugation, screen or membrane filtration, and gravity sedimentation.

As used herein, the term "natural products" is used herein to describe various chemicals, molecules, and proteins including, but not limited to minerals, lipids, proteins, omega-3 fatty acids, essential amino acids, polysaccharides, and vitamins A, B, C, and E, bioactive metabolites, pigments, and the like.

As used herein, the term "algal oil" is used to describe mono, di, and triglycerides of algal origin.

As used herein, the term "extractant" is used herein to describe a liquid used to remove a solute or suspended matter (the system can remove not only solutes but also particles/suspensions) from another liquid.

As used herein, the term "solvent" is used herein to describe a liquid that serves as the medium for a reaction or a medium for the distribution of components of different phases or extraction of components into said solvent.

As used herein, the term "polar solvent" is used herein to describe solvents that have large dipole moments (aka "partial charges"); they often contain bonds between atoms with very different electronegativities, such as oxygen and hydrogen. Non-limiting examples of polar solvents include polar aprotic solvents and polar protic solvents. Non-limiting examples of polar protic solvents include but are not limited to: formic acid, n-butanol, isopropanol, n-propanol, ethanol, methanol, acetic acid, and water. Non-limiting examples of polar aprotic solvents include but are not limited to: tetrahydrofuran, ethyl acetate, acetone, dimethylformamide, acetonitrile, dimethyl sulfoxide, nitromethane, and propylene carbonate.

As used herein, the term "miscibility" is used herein to describe the property of substances to mix in all proportions, forming a homogeneous solution. The term is most often applied to liquids, but applies also to solids and gases. Water and ethanol, for example, are miscible because they mix in all proportions.

As used herein, the term "water miscible solvent" is used herein to describe solvents that are able to form a homogeneous solution with water. Examples of water miscible solvents include, but are not limited to: acetic acid, acetone, acetonitrile, dimethylformamide, dimethyl sulfoxide, dioxane, ethanol, methanol, n-propanol, isopropanol, and tetrahydrofuran.

As used herein, the term "non-polar solvent" is used herein to describe solvents contain bonds between atoms with similar electronegativities, such as carbon and hydrogen (for example hydrocarbons, such as gasoline). Non-limiting examples of non-polar solvents include, but are not limited to: pentane, cyclopentane, hexane, cyclohexane, benzene, toluene, 1,4-dioxane, chloroform, diethyl ether, and dichloromethane.

As used herein, the term "water immiscible solvents" is used herein to describe solvents that are not able to form a homogeneous solution with water. Examples of water immiscible solvents include, but are not limited to: benzene, n-butanol, butyl acetate, carbon tetrachloride, chloroform, cyclohexane, 1,2-dichloroethane, chlorobenzene, methylene chloride, ethyl acetate, di-ethyl ether, heptanes, hexane, methyl-t-butyl ether, methyl ethyl ketone, pentane, petroleum ethers, di-isopopyl ether, trichloroethylene and xylene.

The term "hydrophilic" as used herein, refers to a molecule or substance having an affinity for water; capable of interacting with water through hydrogen bonding; Hydrophilic molecules typically have polar groups enabling them to readily absorb or dissolve in water as well as in other polar solvents.

The term "hydrophobic" as used herein, refers to a nonpolar substance or molecule that does not combine readily with water molecules. Hydrophobic molecules disassociate from water. Water is a polar molecule which means that it carries a partial charge between its atoms. Hydrophobic molecules are molecules that do not have a charge, meaning they're nonpolar. Hydrophobic materials often do not dissolve in water, or in any solution that contains a largely aqueous (watery) environment.

The wag "multi-component suspension" as used herein, refers to a mixture of protein, carbohydrates, lipids and other molecules. In some embodiments, a multi-component suspension comprises of broken down cells, which includes a mixture of protein, carbohydrates, lipids and other cellular debris. In some embodiments, such multi-component suspensions are in an aqueous solution.

As used herein, the term "amphiphilic agent" refers to an agent that modifies the interfacial tension of water; usually substances that have one lipophilic and one hydrophilic group in the molecule; includes soaps, detergents, emulsifiers, dispersing and wetting agents, and several groups of antiseptics. In some embodiments, amphiphilic agents interfere with the hydrogen bonding of another molecule and water.

As used herein, the term "flocculants" or "flocculating agents" or "flocking agents" are used herein to describe chemicals that cause colloids and other suspended particles in liquids to aggregate, forming a floc. Flocculants are used in water treatment processes to improve the sedimentation or filterability of small particles. For example, a flocculant may be used in swimming pool or drinking water filtration to aid removal of microscopic particles which would otherwise cause the water to be turbid (cloudy) and which would be difficult or impossible to remove by filtration alone.

Particles in water finer than 0.1 μm remain continuously in motion due to electrostatic charge (often negative), which causes them to repel each other. Once their electrostatic charge is neutralized by the use of coagulant chemical the finer particles start to collide and agglomerate (combine together) under the influence of Van der Waals's forces. These larger and heavier particles are called flocs.

The following chemicals are used as flocculants: alum, aluminum chlorohydrate, aluminum sulfate, calcium oxide, calcium hydroxide, iron(II) sulfate, iron(III) chloride, polyacrylamide, polyDADMAC, sodium aluminate, and sodium silicate. The following natural products are used as flocculants: chitosan, isinglass, Moringa oleifera seeds (Horseradish Tree), gelatin, Strychnos potatorum seeds (Nirmali nut tree), Guar gum, and Alginates (brown seaweed extracts).

The term "sugar" as used herein, refers to a monosaccharide, disaccharide, trisaccharides, or polysaccharides. Monosaccharides have the general formula $(CH_2O)_n$, in which n is an integer larger than 2. Disaccharides have the general formula $C_n(H_2O)_{n-1}$, with n larger than 5. Polysaccharides include such substances as cellulose, dextrin, glycogen, and starch.

The term "salts", as used herein, refers to any salt or counter ion that complexes with identified compounds contained herein while retaining a desired function, e.g., biological activity. The term "counter ion", as used herein, refers to the ion that accompanies an ionic species in order to maintain electric neutrality. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Pharmaceutically acceptable salts also include base addition salts which may be formed when acidic protons present are capable of reacting with inorganic or organic bases. Suitable pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glutamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the invention. Unless otherwise specifically stated, the present invention contemplates pharmaceutically acceptable salts of the considered compositions.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

The term "saturated" when referring to an atom means that the atom is connected to other atoms only by means of single bonds.

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 1A is a flow chart of standard methods.

FIG. 10A shows 0.1% TSS algae with solvent; FIG. 10B shows 0.1% TSS algae mixed with polyDADMAC surfactant and then mixed with solvent; FIG. 10C shows 10% TSS algae with solvent; and FIG. 10D shows 10% TSS algae mixed with surfactant and then mixed with solvent.

FIG. 13A shows solvent phase TSS after 2 h of settling, FIG. 13B shows the solvent phase TSS after 24 h of settling, FIG. 13C shows the aqueous phase TSS after 2 h of settling and FIG. 13D shows the aqueous phase TSS after 24 h of settling.

FIG. 25A-D shows various effects of pH on zeta potential of egg albumin.

FIG. 25A shows the zeta potential before polymer additions was measured for the three pH levels and was found to be −3.72 mV, −6.58 mV and −25.1 mV for pH 6, 7, and 8 respectively.

FIG. 25B shows further analysis [3] indicates that this system lies in the region marked by a red oval in the generalized pH vs. Zeta-potential curve alluding that the system is well dispersed and a reduction of pH would force the system to arrive at its isoelectric point—which also would lead to floc formation (indicating the possibility of better particle separation/migration from aqueous phase given adequate hydrophobicity is attained).

FIG. 25C and FIG. 25D suggest that under neutral pH conditions, the amount of proteins migrating to hexane phase is optimum.

FIG. 26A-C shows the effect of polyelectrolyte concentration and zeta potential on protein migration.

FIG. 29A show an image of proteins (294×)

DESCRIPTION OF THE INVENTION

Figures 1A, 1B:
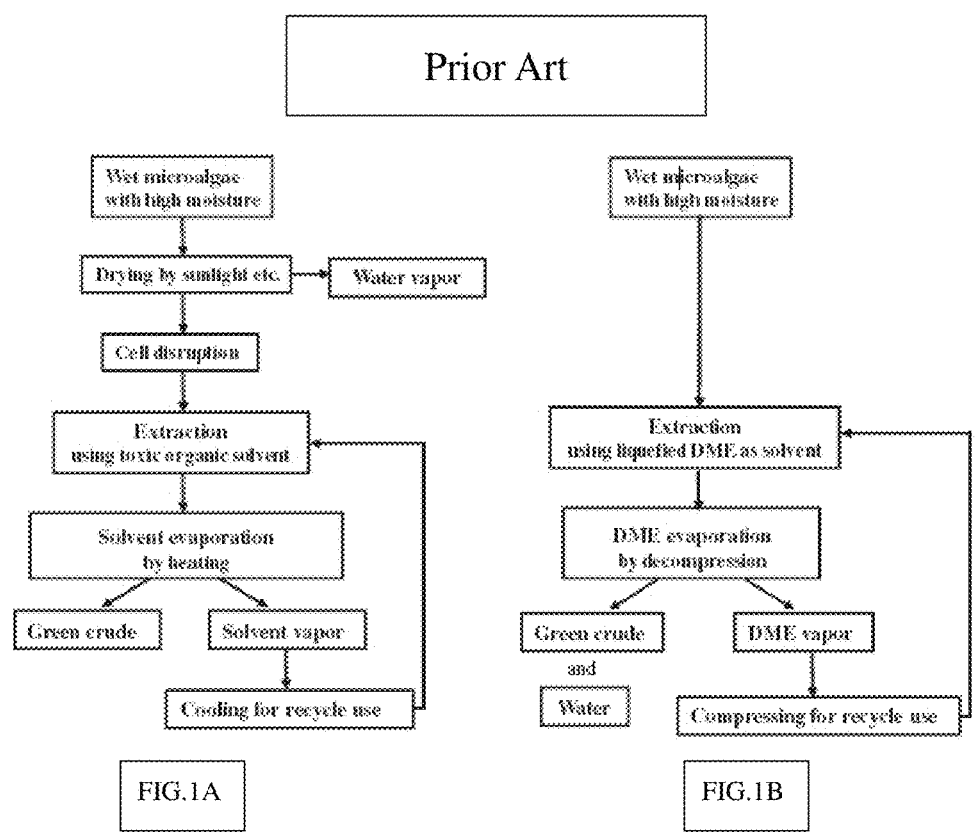
FIGS. 1A&B show a comparison of prior art methods.
FIG. 1B shows a flow chart of the Kanda method which focuses on combined drying, cell disruption description, and solvent extraction in one step [1].

There have been many attempts at processing algae. One reference, United States Patent Application 2010-0261922 [4], discloses centrifuging a wet algal biomass to increase the solid content to between approximately 10% and 40%, mixing the centrifuged algal biomass with an amphiphilic solvent, heating the mixture to produce a dehydrated, defatted algal biomass, separating the amphiphilic solvent from the dehydrated, defatted algal biomass to result in amphiphilic solvent, water and lipids, evaporating the amphiphilic solvent from the water and the lipids, and separating the water from the lipids. The amphiphilic solvent may be selected from a group consisting of dimethyl ether, acetone, methanol, ethanol, isopropanol, butanone, propionaldehyde, and other similar solvents. Other exemplary methods include filtering a wet algal biomass through a membrane to increase its solid content to between approximately 10% and 40% to produce a filtered algal biomass. This reference does not disclose the use of amphiphilic agents in addition to commonly used solvents.

Another reference, United States Patent Application 20100068772 [5], discloses methods for solubilizing algae or algal material to facilitate the recovery of oils or lipids, as well as hydrocarbons and carbohydrates, from algae or algal material. The methods involve contacting algae or algal material with an oxoacid ester or thioacid ester of phosphorus (or a mixture of an oxoacid of phosphorus and/or an alcohol) to solubilize the algae or algal material. These methods optionally comprise bioconversion of the solubilized algae or algal material to form a composition suitable for recovery of oils and non-oil chemicals.

Another reference, United States Patent Application 20100304452 [6], discloses a process for producing biofuels from algae by cultivating an oil-producing algae, extracting the algal oil, and converting the algal oil to biodiesel. Extracting the algal oil from the oil-producing algae may include biologically rupturing cell wall and oil vesicles of the oil-producing algae using at least one enzyme such as a cellulose or glycoproteinase, a structured enzyme system such as a cellulosome, or viruses. This reference does not disclose the use of amphiphilic agents to induce extraction of algae oil.

Another reference, U.S. Pat. No. 6,166,231 [7], discloses a method of separating edible oil from biological material. A biomass slurry containing microbial material in an aqueous suspension is centrifuged and then homogenized. The resulting slurry is fed into a contacting device, such as a packed column, and mixed with a solvent that is immiscible in water (e.g. hexane). The solvent extracts and separates the oil from the biomass slurry. Edible oil is recovered from the solvent and further processed. This reference does not disclose the use of amphiphilic agents to induce extraction of algae oil.

Another reference, U.S. Pat. No. 7,431,952 [8], discloses extraction of oil (i.e. polyunsaturated fatty acids), directly from microbial cells without the need for solvents. After fermentation, the microbial cells are pasteurized, washed and lysed by a mechanical (e.g. homogenization), physical (boiling or drying), chemical (solvents) or enzymatic (cell wall degrading enzymes) technique. The oil is then separated from the resulting cell wall debris by centrifugation, which results in an oil phase (top layer) that can be separated from the aqueous phase (containing the cell wall debris). This reference does not disclose the use of amphiphilic agents to induce extraction of algae oil.

Another reference, Kanda (2010), Fuel 90(3), 1264-1266 [1] discloses using dimethyl ether to extract green crude from high-moisture natural blue-green microalgae (91.0% water content). FIG. 1 shows a comparison of previous methods (A), the Kanda method (B) combined drying, cell disruption description, and solvent extraction in one step. Dimethyl ether is shown to be partially miscible with water, but sufficient to significantly aid in the dewatering process. Dimethyl ether is removed by allowing it to return to its natural gas state at standard pressure (to be reused later). This reference does not disclose the use of amphiphilic agents to induce extraction of algae oil.

Another reference, U.S. Pat. No. 7,749,392 [9], discloses a process of dewatering an aqueous suspension employing a flocculating system comprising treating the suspension with a flocculating amount of a first flocculant and a dewatering amount of a second flocculant, and subjecting the suspension to mechanical dewatering to form a cake, wherein the first flocculant brings about flocculation and assists thickening of the suspension and the second flocculant further dewaters the suspension, characterized in that the second flocculant is a water-soluble or water swellable polymer that is mixed into the suspension in the form of aqueous composition comprising dissolved or hydrated polymer having a Brookfield viscosity of above 30,000 cps (measured at 20° C.). This patent states, "In the dewatering of suspensions it is known to add a high molecular weight, water soluble polymer as a flocculant to the suspension in order to remove the liquid from the suspension and greatly increase the dry solids of the suspension. High molecular weight flocculants may be cationic, anionic, nonionic or amphoteric in nature. The choice of polymeric flocculant will largely depend upon the substrate, which is being treated." This reference does not disclose the use of amphiphilic agents to induce extraction of algae oil.

Another reference, Divakaran (2002) Flocculation of Algae Using Chitosan, *J. Appl. Phycol.* 14, 419-422 [10], discloses flocculation of three freshwater algae, *Spirulina, Oscillatoria* and *Chlorella*, and one brackish alga, *Synechocystis*, using chitosan at pH 4 to 9, and chlorophyll-a concentrations in the range 80 to 800 mg $m^{-3}$, which produces a turbidity of 10 to 100 nephelometric turbidity units (NTU) in water. Chitosan effectively reduces the algal content by flocculation and settling. The flocculation efficiency is very sensitive to pH, and reached a maximum at pH 7.0 for the freshwater species, but at a lower pH for the marine species. The optimal chitosan concentration for flocculation depends on the concentration of alga. Flocculation and settling were faster when higher than optimal chitosan concentrations are used. The settled algal cells are intact and alive, but will not be redispersed by mechanical agitation. The de-algated water may be reused to produce fresh cultures of algae. This reference does not disclose the use of amphiphilic agents to induce extraction of algae oil.

Another reference, Buelna (1990), *Biological Wastes* 31, 211-222 [11], discloses the testing of various flocculants, including polyacrylamides and chitosan, on the recovery of algal biomass. The rationale behind this study was to evaluate if pig waste could be utilized to grow algal biomass that in turn could be used to feed livestock. While this reference does not include recovery of algal oil as a goal, it does show the use of various flocculants described in the invention disclosure. This reference does not disclose the use of amphiphilic agents to induce extraction of algae oil.

DETAILED DESCRIPTION OF THE INVENTION

Microalgae is a promising source of lipids for biofuel production and fatty acid, pigment, separation for nutritional and pharmaceutical production [12, 13]. However, one major problem of lipid extraction from microalgae is caused by the huge amount of associated water [14-16]. Solvent extraction is an important step in lipid separation [17]. However due to large amount of moisture contact between algal cells and organic extraction solvent gets hindered. About 99.9% weight of the algae broth in an algal culture is water [14]. For conventional solvent extraction, a significant portion of this moisture is needed to be reduced during pretreatment [18, 19]. For example, during initial coagulation and sedimentation steps, the moisture content is reduced to approximately 90% [14]. However further reduction of moisture requires costly centrifugation and drying operations [14, 20, 21] and is impractical due to high energy requirements [20, 22, 23]. What is needed is a technique designed to maximize migration of algal cells to a solvent fraction while simultaneously displacing water in a separate fraction.

In one embodiment, the invention contemplates a method for the extraction of algal oil comprising: a) providing: i) algae cells comprising algal oil and a hydrophilic cell surface; ii) an amphiphilic agent capable of converting said hydrophilic cell surface to a hydrophobic cell surface; and iii) an extractant; b) adding said amphiphilic agent to said algae cells under conditions such that said hydrophobic cell surface is created, and c) purifying said algal oil with said extractant. In one embodiment, said amphiphilic agent is monomeric, oligomeric or polymeric forms of diallyldimethylammonium chloride, sodium 4-styrenesulfonate, or 3-(1-Pyridinio)-1-propanesulfonate. In one embodiment, said algal oil is released in the absence of homogenization. In one embodiment, said method further comprises using a homogenizer to release said algal oil from said algae cells. In one embodiment, said method further comprises purifying said released algal oil with said extractant. In one embodiment, said algae cells are *Nannochloropsis oculata* and *Chlorella vulgaris* cells. In one embodiment, said extractant comprises non-polar solvent.

Solvent Phase Algal Migration (S.P.A.M.) or Low Energy Algal Dewatering Extraction and Recovery (L.E.A.D.E.R.) Process: A Technique for Dewatering Microalgae Efficient microalgae dewatering is a major problem that continuously plagues industrial-scale processing of microalgae metabolites for commercial use. Large scale cultivation of algal biomass is typically produced with a high volume of water (<95%). As a result, harvesting concentrated microalgal cultures presents a significant economic challenge to industries such as algae-based fuels that are critically dependent on improvement of techniques and practices designed to remove algae from water. One promising strategy is the Solvent Phase Algal Migration (S.P.A.M.) process, which is a technique designed to maximize migration of algal cells to a solvent fraction while simultaneously displacing water in a separate fraction. This investigation evaluates the S.P.A.M. dewatering performances of various factors in a comparative study.

Introduction

Beginning with its utilization as a natural source of food in the biosphere, algae has played a significant role in the sustainability of basic life forms as well as advanced civilizations [13, 24]. Some techniques developed centuries ago based mainly on general biological principles for growing and harvesting algae on a large scale are still widely used today. Microalgae in particular have demonstrated their versatility to society as a platform for generating a myriad of desirable metabolite products such as polyunsaturated fatty acids (PUFAs), astaxanthin and bioactive compounds [25, 26]. Several industries such as pharmaceutical, cosmetic, and animal foodstuffs depend on vast quantities of algal biomass for production of intracellular and extracellular metabolites each year to generate revenue [27]. The energy industry in particular is positioned to capitalize on the popularity in biofuels production. As a result of the peak in public interests of algae as a natural source of renewable energy development of thermochemical and biochemical conversion technology is rapidly expanding [12, 28]. There are several benefits of algal biofuel production for agriculture that make their utilization an attractive alternative [29]. For instance, it helps the US government to achieve the goal of producing its targeted amount of alternative fuel by 2030 [30]. Algal biomass is typically grown at relatively low concentrations for industrial purposes [14, 31]. Dewatering biomass is the most significant nuisance to providing algal based products to consumer markets at affordable cost [32]. Energy efficient and economically constrained optimization of this downstream process is the key to developing algal biofuel at levels comparable to traditional fossil fuels supplies [33]. The goal of any downstream process for harvesting/dewatering biomass from a dilute algal suspension to a slurry or paste is to facilitate the recovery of biomass for the subsequent extraction of bio-oil. This step is extremely important in the conversion of microalgae to biofuel because once the oil is extracted it must undergo an additional transesterification process which can hinder conversion efficiency in the presence of excess water. Because of its dilute nature (0.5 gram of whole cell biomass per unit of volume of liquid in open raceway ponds) and high stability of colloidal properties, dewatering microalgae suspensions can account for a significant portion of the cost for downstream processes [34]. Dewatering techniques for algae are typically based on two main types of separation: physical methods and chemical methods. Several strategies which have been employed for the dewatering of algae harvest have been investigated and compared for their ability to separate water from products [22, 32]. Some robust methods may not be suitable for delicate microalgae species. In addition, the viability and stability of the cells during storage may be influenced by the harvesting method [35].

Recovery of microalgae biomass were studied in traditional unit operation techniques such as centrifugation, filtration, flotation, sedimentation, electrocoagulation, and flocculation in addition to novel harvesting techniques [32]. Some work has been reported on the performance of combined dewatering techniques. For instance, any combined systems use pressing and screening belts which facilitate rapid processing through continuous operation. However, very little information was found related to the combination of solvents and algal surface modifiers. Several review of microalgae harvesting techniques have compared microalgae harvesting techniques such as centrifugation, precipitation, ion exchange, tangential flow filtration, flotation, sonication and electrodialysis [36-38]. Their reviews suggested the use of chemical precipitation and centrifugation as the only economically viable options for recovery of microalgae from suspension. These harvesting techniques focused mainly on open pond cultivation systems characterized by very dilute final total solid concentrations. Updated reviews have been reported by various other researchers which include biomass cultivated via photobioreactors exhibiting higher cell densities [38, 39]. Engineering manipulation of the biological properties associated with algae based systems have steadily made incremental improvements in the development of downstream harvesting techniques processes [40]. A new dewatering process which significantly reduces economic and efficiency barriers is warranted. Therefore the potential deployment of solvent phase algal migration for commercial algal biomass harvesting for biofuel production systems must be considered.

Objectives

In Example 1, a process is described that combines the chemically based separation ability of algal surface modifiers and solvents to migrate algal cells away from water was studied for its ability to dewatering algae. Example 1 investigates the effect of organic polymer polyelectrolyte algal surface modifiers on algae species *Nannochlorposis Oculata*. The performance of each dewatering combination will be evaluated quantitatively by the solid content of the recovered microalgae in the water and solvent liquid fractions.

Data Analysis
Experimental Design

The results of the methods described in Example 1 study were obtained by data generated by Design Expert® software using a 25 mixed level factorial designed experiment with two replications. Each experimental unit was sampled randomly from the water layer and the organic solvent layer. The data from the methods in Example 1 was used to evaluate the effect of various combinations of high and low design factors of the process. The four responses used in the data analysis were moisture content, dry weight, algal mass in fluid layer, distribution of dry solids content. Table 1 lists the five design factors used to statistically measure and evaluate the experimental responses (Table 1):

TABLE 1

| Factor Reference Table | |
| --- | --- |
| 1 | Surface Modifier Type |
| 2 | Surface Modifier Concentration |
| 3 | Solvent Fraction |
| 4 | Settling Time |
| 5 | Initial Algal Broth Concentration |

The statistical results are used to describe the influence of the design factors on each response variable.

Moisture Content Analysis

Figure 2:
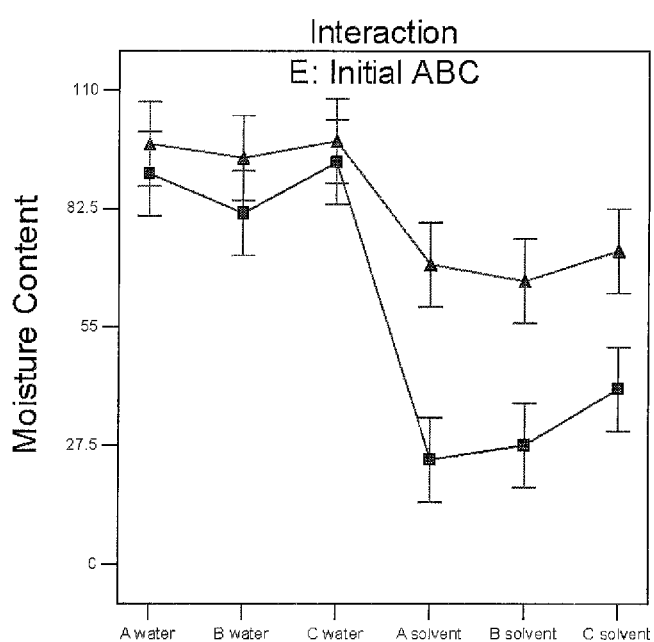
FIG. 2 shows moisture content analysis at 25% solvent: broth (S:B) ratio (E1—0.1% initial ABC; E2—10% initial ABC).

There were significant difference among moisture content ranges of the water phase (53.43% to 100%) compared to moisture content levels of the solvent phase (0.00% to 89.52%). However, there was no statistical difference between the three types of surface modifying agents within the water layer. There was also no difference (<0.05) between types of surface modifying agents for the solvent layer averaged. FIG. 2 summarizes the statistical difference in the dewatering characteristics of the solvent phase based on moisture content analysis. The water phase analysis showed no differences in moisture content among the three surface modifiers and also no differences in moisture content for high and low level of initial algal broth concentration. In contrast, all three surface modifiers demonstrated significantly lower moisture content at the initial algal broth concentration 0.1% for solvent phase. In the solvent phase analysis, the largest difference (<0.05) occurred for surface modifier A.

Figures 3A, 3B:
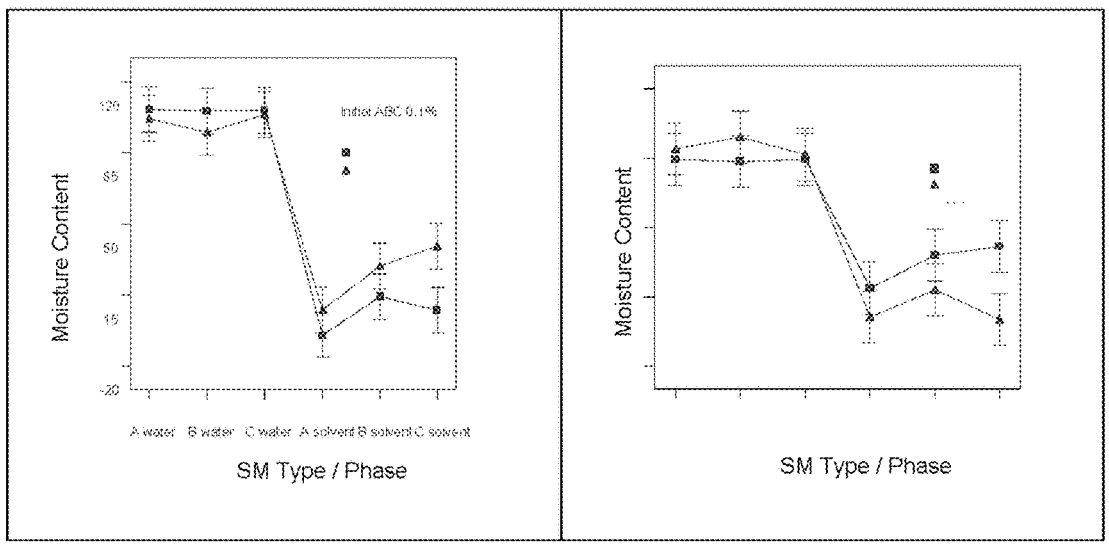
FIG. 3A shows moisture content analysis for 75% S:B ratio and 0.1% Initial ABC versus settling time (1 hr migration time (red); 24 hr migration time (green).
FIG. 3B shows moisture content analysis for 75% S:B ratio and 10.0% Initial ABC versus settling time ((1 hr migration time (red); 24 hr migration time (green).

Moisture content analysis for both levels of initial algal broth concentration at 75% solvent:algal broth (S:B) ratio versus settling time was examined. The only statistical difference at the alpha=0.5 level for settling time occurred for surface modifier "C". The highest moisture contents were observed for the 24 hour settling at an initial algal broth concentration of 0.1% (FIG. 3A). However, under conditions of 10% initial algal broth concentration (FIG. 3B) the higher moisture content was achieved by the 1 hour settling time.

Dry Solids Content Analysis

Figure 4:
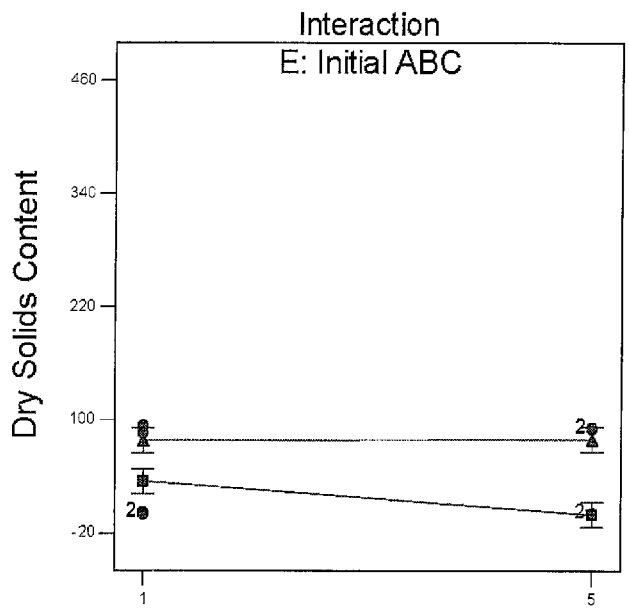
FIG. 4 shows dry solids content of the aqueous phase for 25% S:B ratio and 1 hour settling time (E1—0.1% initial ABC; E2—10% initial ABC).
Figure 5:
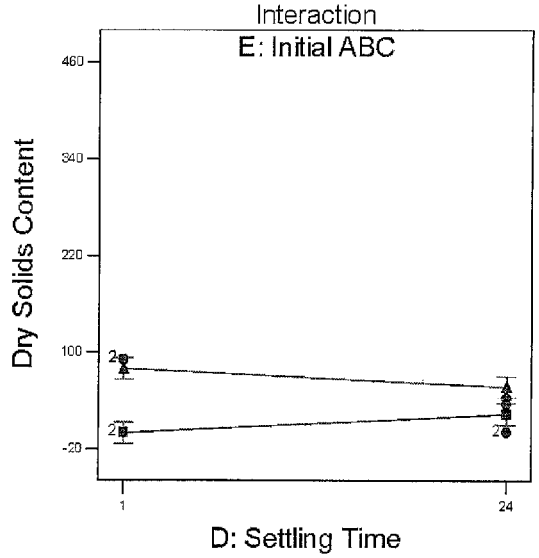
FIG. 5 shows dry solids content of the aqueous phase for 25% S:B ratio vs. settling time (E1—0.1% initial ABC; E2—10% initial ABC).
Figure 6:
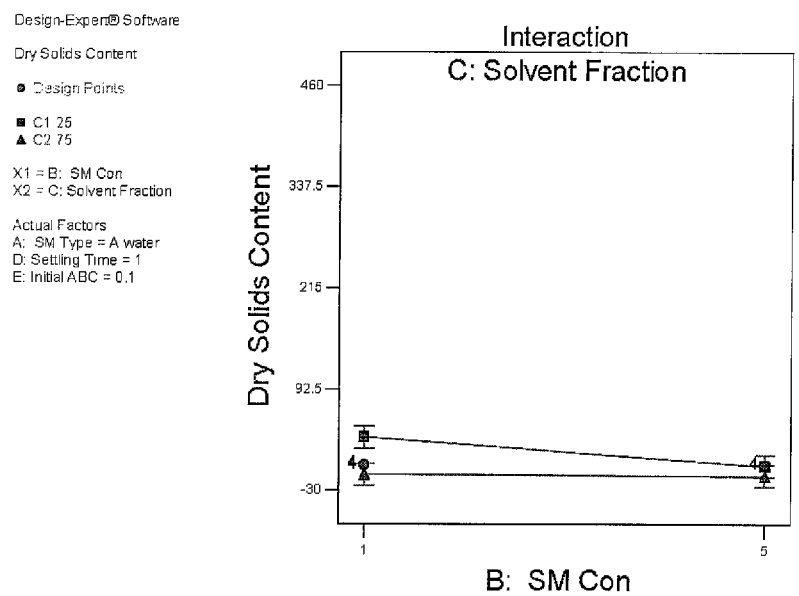
FIG. 6 shows dry solids content of the aqueous phase for 1 hour settling time (S:B ratio vs. surface modifier concentration) (C1—25% S:B ration; C2—75% S:B ratio).
Figure 7:
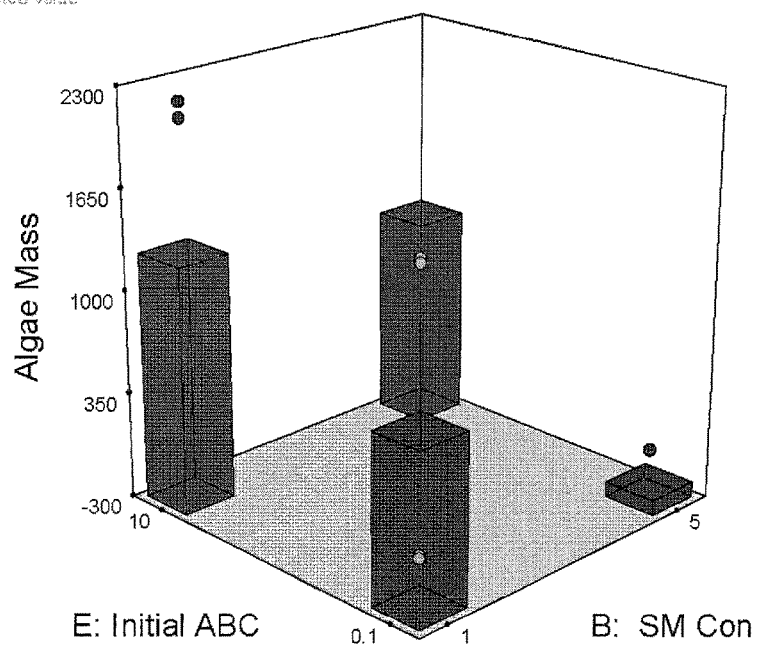
FIG. 7 shows water phase quantity of algal mass (initial concentration vs. surface modifier concentration).

Dry solids content refers to the quantity of soluble and insoluble algal biomass measured after drying at 105 degrees C. per unit volume of medium. To account for all biomass in the system an analysis of the algae biomass in both the water phase and solvent phase in terms of dry solids content was measured as grams per liter. The dry solids content levels for all values of the aqueous phase ranged from 0.00 to 94.0 g/L. While the dry solids content levels of the solvent layer spanned from 0.00 to 452.0 g/L for all values (FIG. 4 and FIG. 5). The affect of adding 1% (w/w) of surface modifier type "A" resulted in a significantly higher quantity of dry solids content for initial algal broth concentration 10% in comparison to initial algal broth concentration 0.1% measurement of the water phase. After one hour settling time, the difference in dry solids content is even greater for 5% surface modifier concentration than for 1% surface modifier concentration at 25% S:B ratio and one hour settling time (FIG. 4). Similar differences in dry solids content occurred for the one hour settling time between initial algal broth concentration for the 25% and 75% S:B ratio experiments, however no change was detected for the 24 hour settling period (FIG. 5 and FIG. 6) at either S:B. ratio. There was no significant difference in algal mass levels of the water layer (0.00 to 1949.25 mg) compared to dry solid content levels of the solvent layer (0.00 to 10170.0 mg) overall. Both levels of the settling time factor in combination with 10% initial algal concentration and 1% surface modification exhibited the highest retention of algal mass in the water layer for 25% S:B ratio. The lowest level of algal mass in the aqueous phase was achieved by 5% concentration of surface modifier type "B" occurring at 0.1% initial algal broth concentration (FIG. 7).

Figure 8:
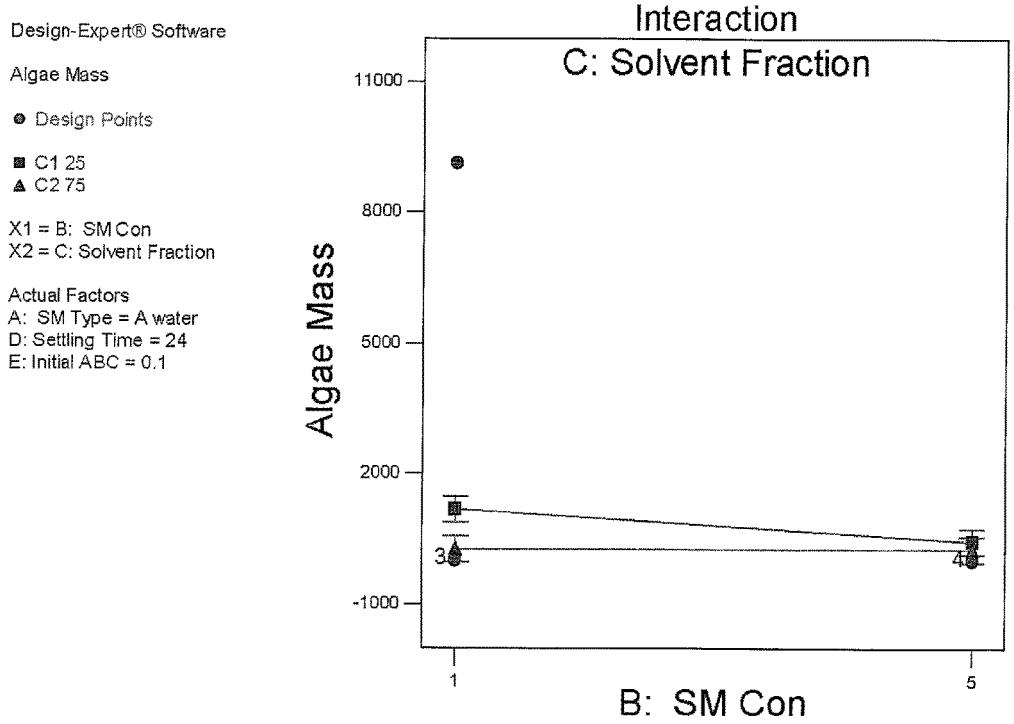
FIG. 8 shows water phase quantity of algal mass for 24 hour settling time and 0.1% initial ABC (S:B ratio vs. surface modifier concentration) (C1—25% S:B ration; C2—75% S:B ratio).

After 24 hours of settling time, 25% S:B ratio was significantly higher than 75% S:B ratio using 1% surface modifier in the water phase in the environment of initial algal phase concentration at 0.1% (FIG. 8).

Distribution of Dry Solids Content Analysis

The calculation for the distribution of dry solids content was performed on data generated from the measurements of algal biomass. These distributions ranged in value from 0.0% to 100%. There were significant differences in distribution of dry solids content of the water layer compared to the distribution of dry solids content of the solvent layer for several combinations of factors. The largest differences for the system occurred for the high and low levels of solvent-to-broth ratio (25% vs. 75%) under the conditions of 24 hour settling with Surface modifier type "B" starting with Initial Algal Broth Concentrations of 10.0%. Within this combination of factors an even finer difference was detect between 1% and 5% concentration of surface modifier. Table 2 summarizes the combination of factors with significant differences between the distribution of dry solids. The remaining combinations not listed showed no statistically significant differences within treatments combination or between treatment combinations determined from ANOVA analysis ($p<0.05$).

TABLE 2

Distribution of Dry Solids Content Significant Differences Comparison for Initial Algal Broth Concentration

| SM Type | SM Conc. (%) | Water/Solvent Layer | Settling (hr) | S:B Ratio (%) | Significant Difference Between |
|---|---|---|---|---|---|
| A, C | 5 | both | 1 | 75 | 0.1% vs 10.0% |
| A, C | 5 | both | 24 | 75 | 0.1% vs 10.0% |
| B | 1 | both | 24 | 25 | 0.1% vs 10.0% |
| B | 5 | both | 24 | 25 | 0.1% vs 10.0% |

Figure 9:
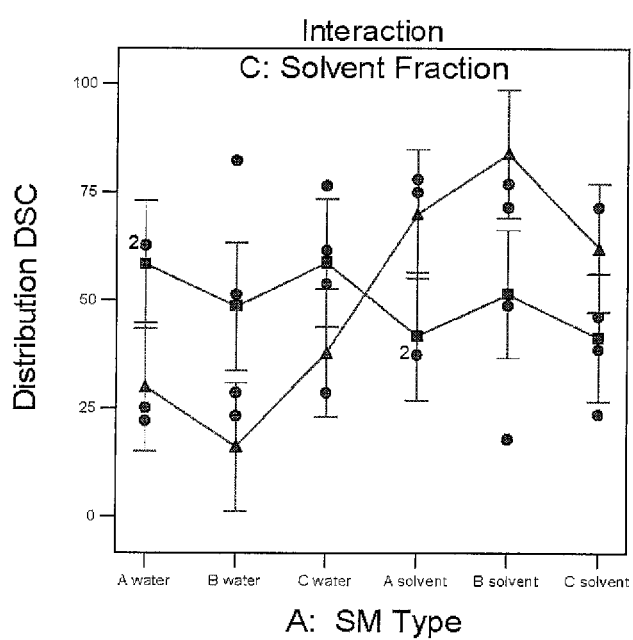
FIG. 9 shows the effects of 5% surface modifier B interaction in both water layer and solvent layer (C1—25% S:B ration; C2—75% S:B ratio).
Figures 10A, 10B, 10C, 10D:
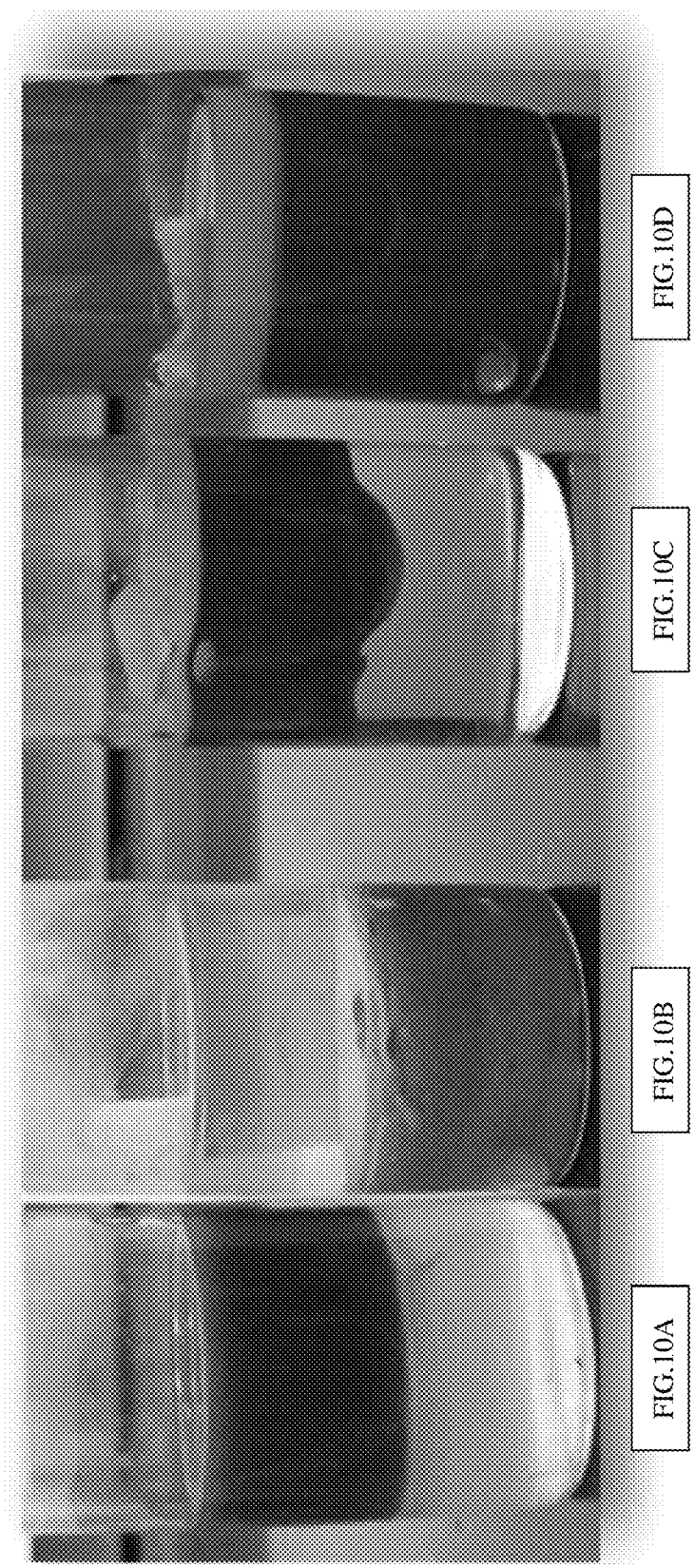
FIG. 10A-D shows the effect of surfactant on miscibility of algae with chloroform.

A specific case analyzing the difference in the distribution of dry solids content for different types of surface modifiers is graphically summarized in FIG. 9.

Factors which may influence moisture content of algae-in-water suspension systems were investigated in this research. From the assessment of this data, algal cell surface modification does not appear to have a clear uniform set of optimized parameters. Rather the best combination of settings depends on the response solicited by the analysis. For instance, a given surface modifier type and concentration producing a low algal mass level in the water phase may not always correspond to high algal mass levels in the solvent phase. In further study, it may be useful to develop optimization models for each response variable to describe the interaction of the system in more detail. The conclusions of this study are categorized in terms of the four response variables.

Moisture Content Analysis

The type of surface modifier had the most significant influence on moisture content in the water phase followed by initial algal broth concentration. Surface modifier "B" demonstrated the greatest amount of dewatering among the surface modifiers. The analysis of the moisture content indicates that the surface modifier concentration is not an important factor for any of the surface modifier types in determining algal cell surface modification. Therefore, to save money and resources during pilot-scale and industrial dewatering processes only 1% concentration of surface modifier should be employed. Additional factors which have demonstrated influence on moisture content to a lesser degree include synergistic combinations of factors surface modifier type, initial algal broth concentration, and solvent-to-broth ratio, respectively.

Dry Solids Content Analysis

The dry solids content (total solids) of an algal dewatering system consequentially affects some reference calculations dependent on algal mass used for quantification of this type of system. Therefore any influences on its change in value caused by manipulation of dewatering process parameters are considered important. As expected, dry solids content is mainly influenced by the initial algal broth concentration. More specifically, the 10.0% initial algal broth concentration provides a higher quantity of dry solids content per volume of sample than the 0.1% initial algal broth concentration. The higher quantity of dry solids at 10% may correspond to an increased algal cell to cell proximity that accounts for the differences observed in interaction with other dewatering process parameters.

Algal Mass in Each Fluid Layer

The solvent-to-broth ratio proved to be the most dominant factor in determining a response for algal biomass in each phase. However, it is important to note that even with the inclusion of the other significant factor, initial algal broth concentration, in addition to the synergistic interaction of surface modifier concentration, these factors only contribute less than 17% of the total variability in determining values for algal mass in both layers. Therefore the algal mass numbers should not be relied on for describing the accuracy in sensitive analyses.

Distribution of Dry Solids Content

This analysis of the distribution of dry solids content proposes that the individual factors of surface modifier concentration, Solvent-to-broth ratio, settling time, and initial algal broth concentration all do not significantly play a role for determining values for this response. Surface modifier type and the interaction of surface modifier type with surface modifier concentration work together to represent 47% of the variability contributing to changes in distribution of dry solids content. This provides evidence that the process described herein is an effective microalgae recovery process suitable for biofuel based production systems.

Moisture Displacement and Simultaneous Migration of Surface-Functionalized Algae from Water to an Extraction Solvent Using Ionic Polyelectrolytes Effective moisture removal and the ability of algal biomass to be compatible with lipophilic solvents are key to making the algal lipid extraction processes economically viable. Example 2 describes a simple technique to chemically remove moisture from algal water while forcing above 95% of the algal cell mass to migrate to a (hydrophobic) lipid extraction solvent. The technique is based on functionalization of algal cell surface with a water-soluble cationic polyelectrolyte, Poly(diallyldimethylammonium chloride) (Poly-DADMAC) that has hydrophobic ligands in its structure. Studies indicate that algal cells continued to displace moisture even after migrating into the solvent phase—continuing to perform the chemical drying step. The general results indicate that the technique could be extended to systems that require separation of particles with charged surfaces—by using a surface active ionic polyelectrolyte with appropriate charge and ligand combination(s).

During preliminary investigations, it was observed that algal broth treated with ca. 1% (w/w) polyDADMAC cationic polyelectrolyte repelled water and migrated to the organic solvent (FIG. 10A-D). Based on these encouraging results, there was a desire to elucidate the effect of the molecular weight of the surfactant, solvent effects and time on moisture removal and solid separation characteristics of surface modified microalgae. Example 2 describes methods of this investigation.

Results and Discussion

Figure 12:
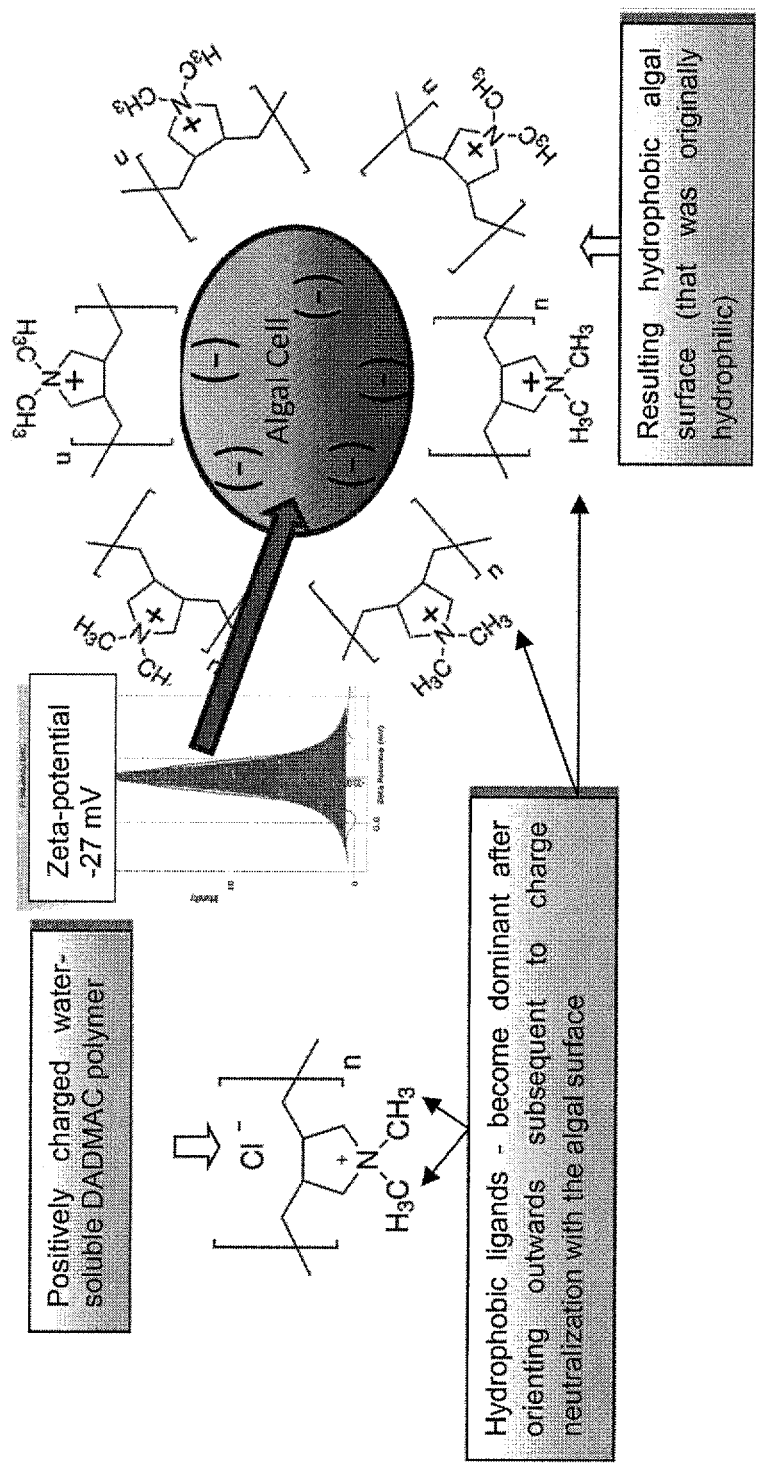
FIG. 12 is a pictorial depiction of possible mechanism e hydrophilic algal surface (or chemical moiety) can be functionalized to be hydrophobic via cationic polymer attachment (or vice versa) by modulating the ligands of the surface active polymer.
Figures 13A, 13B, 13C, 13D:
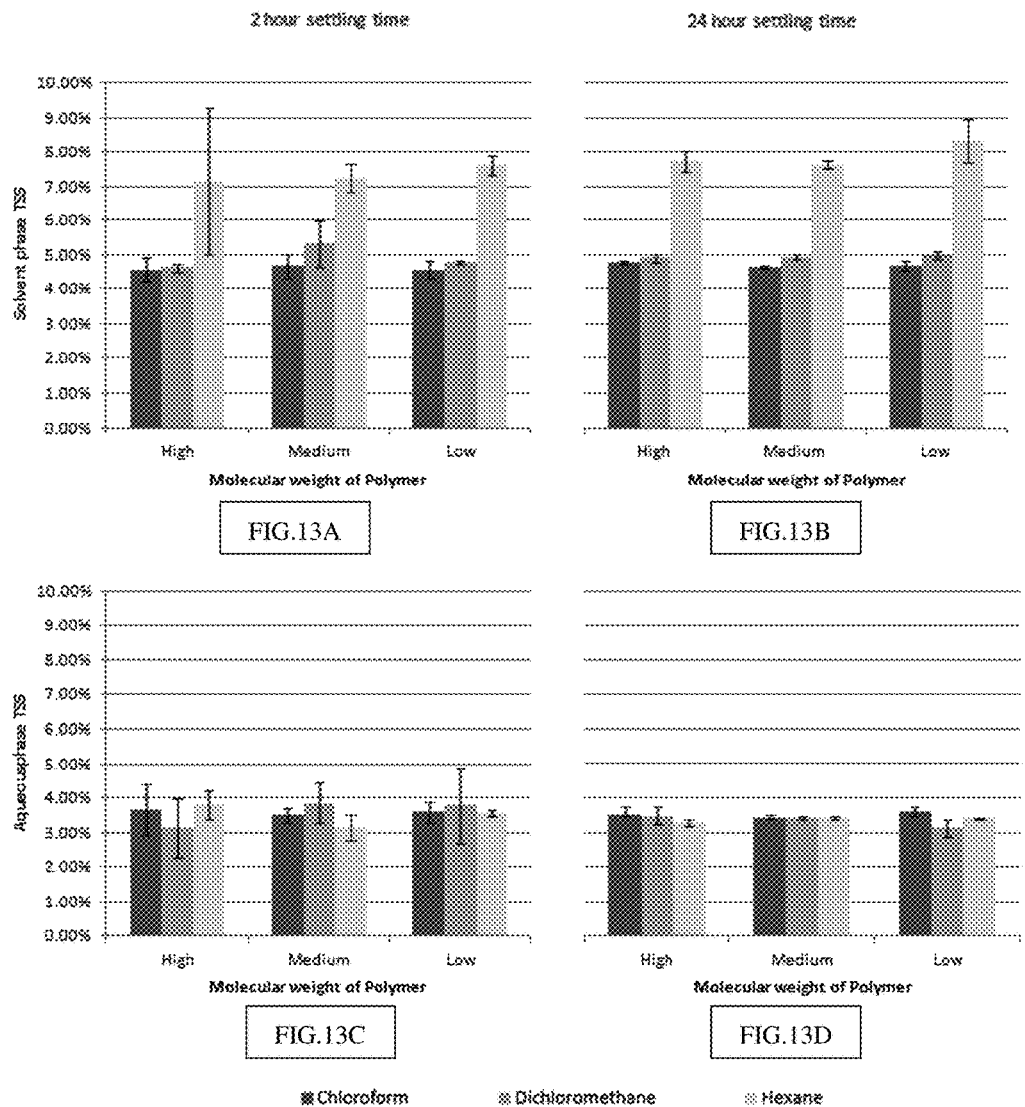
FIG. 13A-D shows TSS in aqueous and solvent phases.

It is possible that the cationic nature of poly-DADMAC and the presence of hydrophobic ligands are responsible for the cell migration behavior that was observed. Poly-DADMAC is polar enough to be soluble in (algal) water [41]. However, once algae are encountered, positively-charged ends of Poly-DADMAC may get attached onto the negatively-charged algal cell-wall (with a measured zeta potential of −27 mV) exposing the hydrophobic ligand ends to the exterior (FIG. 12). This makes the algal cell surface hydrophobic—now repelling water. The organic solvents (i.e., hexane, dichloromethane and chloroform) that were used were hydrophobic and thus, the now "hydrophobitized" algae may "attract" and migrate toward the solvent molecules. Since the solvent and water are immiscible, aqueous-phase gradually displaces to the top (due to the density difference between lighter water and heavier chloroform and dichloromethane or vice versa in the case of lighter hexane) leaving algal cells behind in the solvent phase.

FIG. 13A-D shows the TSS in aqueous and solvent phases after 2 or 24 h settling times. It is apparent that the solvent has a significant effect on the TSS in solvent layer. Hexane shows higher Total suspended solids content compared to other two solvents. Molecular weight of the polymer or the settling time does not play a significant role in deciding the TSS in solvent phase. None of the tested parameters; i.e. solvent, polymer chain length or settling time had an effect on the TSS in aqueous phase.

Figures 14A, 14B:
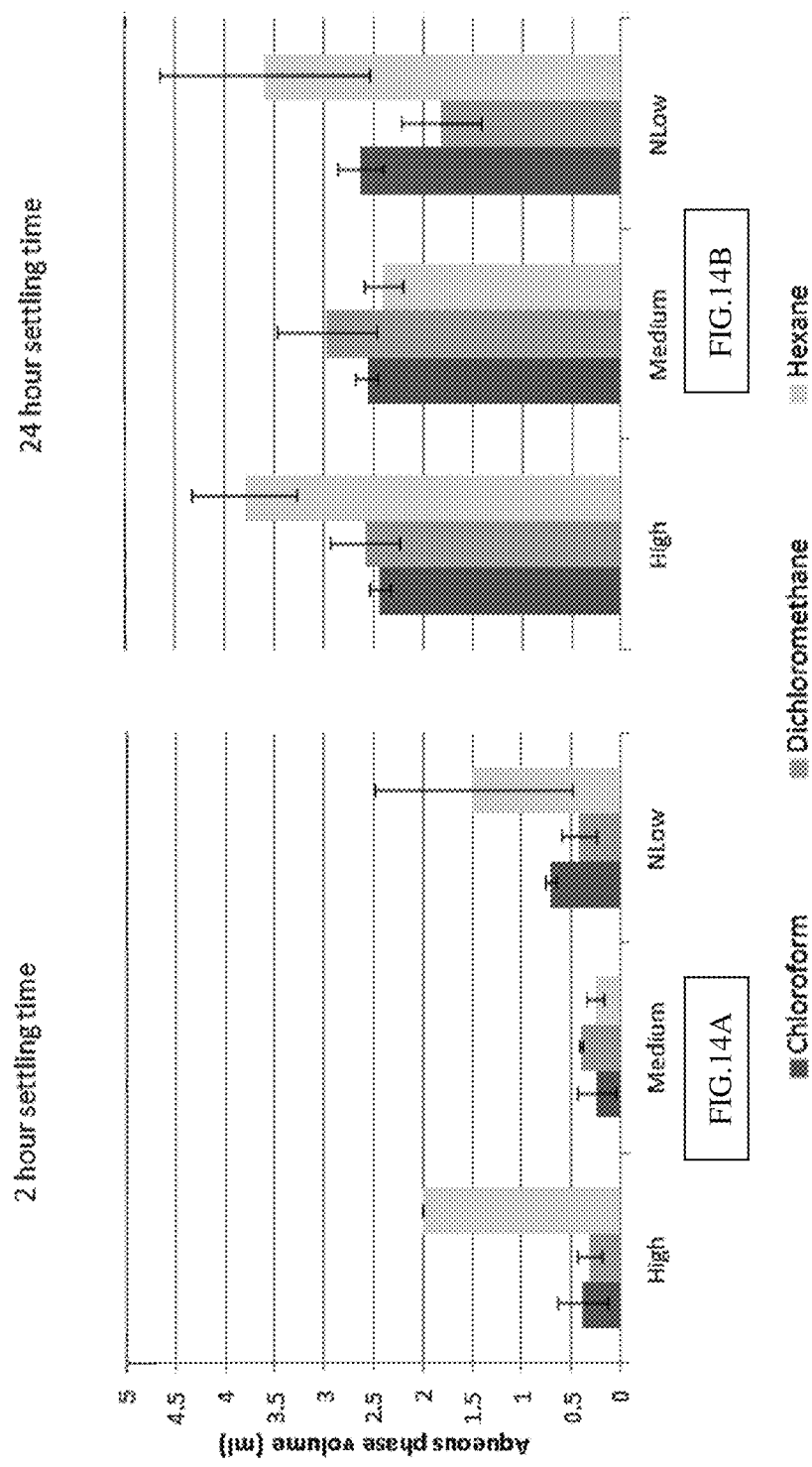
FIGS. 14A&B shows the volume of aqueous phase after 2 h settling time (FIG. 14A) and after 24 h settling time (FIG. 14B).

From above results, it is clear that there is a decrease of TSS in aqueous phase when solvent is introduced (from 10% TSS). However, it is necessary to consider the volume fractions of the two phases. FIGS. 14A&B illustrates the variation of volume of the aqueous phase after separation (note that the total system volume is 20 ml). After 2 h of settling, the volume of aqueous phase was about 5% of the total volume of the mixture. However, after 24 h of settling, it was possible to achieve up to 35% removal of aqueous phase. This implies that moisture i.e., water that was embedded in cytosol, continues to get removed from the system even after the cells have migrated into the solvent phase. It should be noted that the broader error bars are attributed to variability associated with separating the two layers with adequate precision. However, it is noted that the error values are relatively small when compared with the total volume of the mixture.

Figure 15:
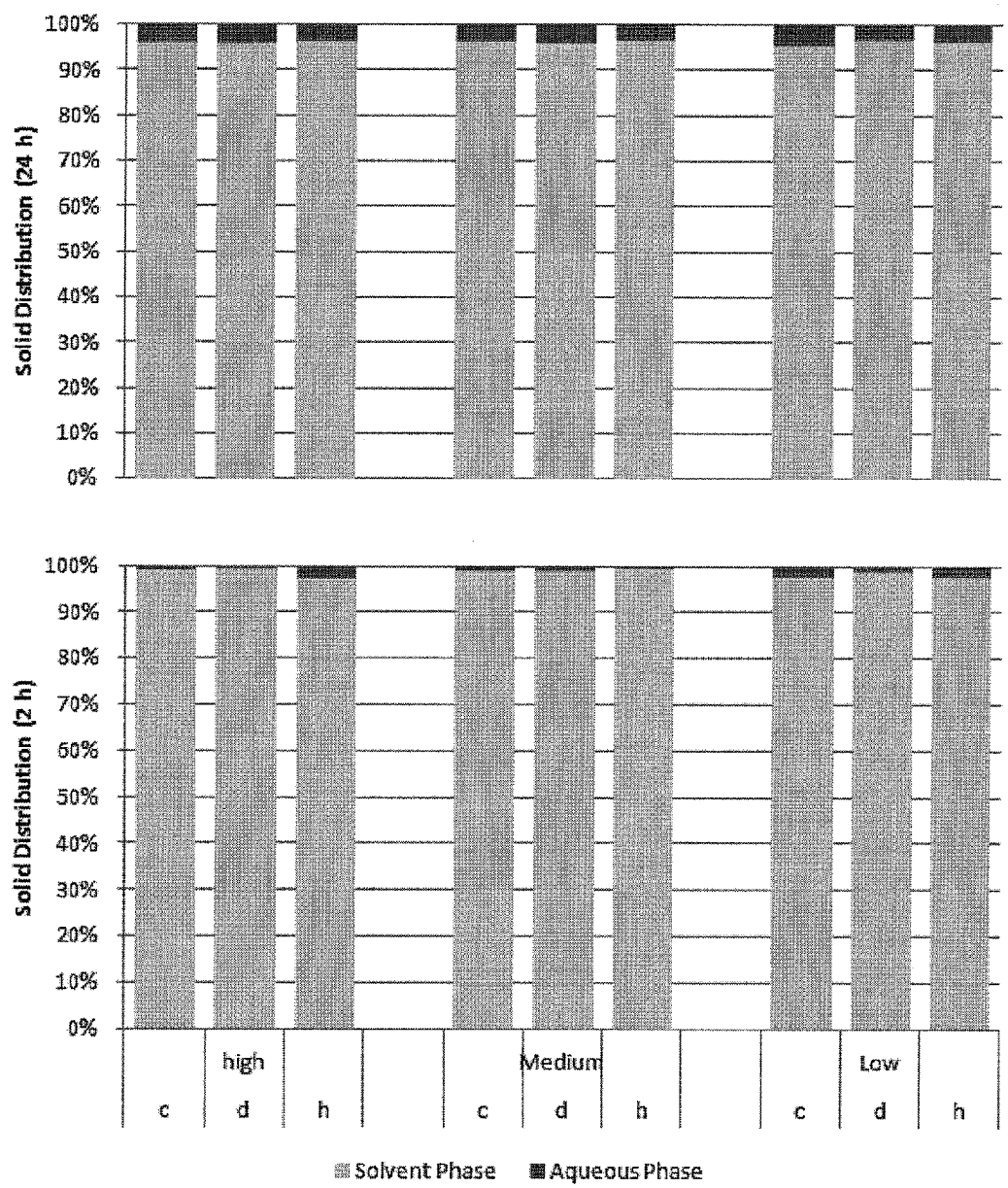
FIG. 15 shows solid content in each phase as a percentage of total solids in the mixture. Independent axis represents combinations of surfactant molecular weight (High, Medium and Low) and solvent (c: chloroform, d: dichloromethane, h: hexane).

The amount of total solids in each phase (calculated using equations (2) and (4)) are depicted in FIG. 15. It is clear that the amount of solids in the aqueous layer is negligible after settling. This implies that this polyDAD based algal cell migration system is quite effective.

In one embodiment, the present invention contemplates a method of algal oil isolation as described in Example 3.

Conclusions

Migration of algae treated with a cationic polyelectrolyte, PolyDADMAC surfactant from aqueous phase to organic phase was investigated as a means of removing moisture. All three organic solvents responded positively to the cell migration scheme with over 95% (w/w) of cell migration from aqueous phase to solvent phase. Of the three solvents, hexane performed best by allowing the highest amount of cell migration. It was observed that the molecular weight of surfactant does not have an impact on the degree of cell migration or the quantity of water displaced. It was also noted that the system continued to displace moisture even after the cells had migrated into the solvent phase (continuing to perform the chemical drying). The ionic polyelectrolyte based particle migration technique could be adopted to separate particulate matter with charged surfaces using a polyelectrolyte or a surface active agent with appropriate ligand/charge combination(s). The feasibility of using this technique in bioseparations, especially, in high value product separation from complex biological fluids should be further investigated.

Separation of Proteins Via Ionic Nanomaterials (S.P.I.N.)

In one embodiment, the invention relates to a technique that can be used to separate proteins from an aqueous mixture by using surface active ionic materials (monomeric, oligomeric and polymeric including those at nanoscale) that have hydrophobic ligands. The water-soluble ionic electrolytes, once bound to protein surface, expose the hydrophobic ligands/branches to the exterior making the protein-electrolyte ensemble hydrophobic. Now the hydrophobic ensemble migrates away from the aqueous phase to an adjacent hydrophobic solvent (that is immiscible with aqueous phase). The protein electrolyte interaction can be initiated by using an electrolyte with opposite charge to the protein or by making the protein attain the required charge by pH adjustment such that the pH is above or below the protein's isoelectric point). By using this technique, any material with a surface charge could be selectively separated from a bulk mixture that has matter with opposing (surface) charges or charge neutral matter. The results, as described in Example 4, indicated that this technique can be used to recover proteins from water on an industrial scale and can be used as primary step for protein recovery before further purification. This Separation of Proteins via Ionic Nanomaterials (S.P.I.N.) process is an advancement to the S.P.A.M. (Solvent Phase Algal Migration) process that has already been disclosed (which has been renamed to Low Energy Algal Dewatering Extraction and Recovery, L.E.A.D.E.R.).

Using this technique, proteins that occur in large water masses (such as those obtained via microbial or algal bioprocessing) can be easily separated from the bulk mixture. The need to remove large quantities of water (~99% w/w wet basis), from biological processes (i.e., dewatering) is a significant technical challenge that the industry faces today. A chemical dewatering technique that can remove a significant portion of this water (>95%) without using any heat can revolutionize the bioprocessing Industry. The energy and cost savings would be significant. The technique will also be helpful in isolating proteins from the burgeoning algal Industry where significant quantities of water have to be dealt with.

1. This is a chemical dewatering technique that occurs without any heat involvement. So, the energy and cost savings would be significant;

2. The technique could be used for selective separation of proteins from a bulk mixture based on unique surface charges that the protein possesses. The technique can modulate the surface charge of proteins (based on pH variation above or below the isoelectric point) such that proteins can selectively carry a unique surface charge as opposed to the bulk and use this unique surface charge to selectively bind onto electrolytes with complementary electrolytes to separate the protein(s) from the bulk medium.

3. The electrolyte-bound proteins migrate to a solvent phase that is immiscible with original aqueous phase. So, further fractionation becomes much simpler.

4. Proteins migrated to solvent phase forms an instantaneous gel (likely due to partial structural unfolding) which makes removal of aqueous phase (with remaining bulk mixture) easy and simple.

5. The electrolytes (or protein) could be recovered by using an isopropanol wash. In such instance all protein precipitates while the electrolyte stays in isopropanol phase.

6. The S.P.I.N. process could be easily integrated into current bioprocessing systems such that the process would separate a bulk medium to protein rich and protein-lean streams for further purification.

The use of ionic electrolytes to migrate proteins into organic solvents is believed to be an unprecedented development. In limited literature where organic solvents were used for protein separation, it has been reported that proteins form an intermediate layer between water and the organic solvent. In contrast, S.P.I.N. causes proteins to entirely migrate into the organic solvent-forming an easy to separate gel.

The current invention can be practiced for primary protein recovery from microbial, algal streams, or other streams of multi-component suspension of broken down cells.

This work is an advancement of Solvent Phase Algal Migration (S.P.A.M.) process, described previously. Proof-of-concept studies on migration of the model protein, albumin, using polymeric and monomeric versions of diallyldimethylammonium chloride (DADMAC) cationic polyelectrolyte are included herein. These studies evaluated the impact of polymer type, polymer concentration, pH of the medium, settling time and temperature on the degree of protein migration from aqueous phase to hexane. The experiments, described in Example 4, prove that both types of DADMAC can successfully migrate albumin from aqueous phase to electrolyte surfactant from aqueous to organic phase. Lipids will directly move to hexane phase. Proteins, depending on pH could be moved to hexane or retained in aqueous phase. By modulating pH, the system facilitates which particles to mobilize. Once migrated, the protein-electrolyte ensembles form a gel in solvent phase that is distinct and easy to separate from aqueous phase.

Polyelectrolyte Based Technique for Sequestration of Protein from an Aqueous Phase to an Organic Solvent Separation of proteins from a complex multi-component suspension of broken down cells is challenging. In this regard, a technique that is capable of distinguishing proteins from other major cellular components (such as carbohydrates, lipids and other cellular debris) could immensely simplify downstream processing. In one embodiment, the current invention relates to the ability of using the inherent zwitterioninc properties of proteins to attach amphiphilic cationic electrolytes so that proteins can be extracted from an aqueous suspension into a water-immiscible organic solvent. Herein, the separation of egg albumin (model protein) from aqueous suspension to adjacent hexane phase using poly-(diallyldimethyleammonium) chloride (Poly-DADMAC) is shown. Results in Example 5 show that, under optimum pH and polymer concentrations, proteins can be successfully migrated from water to the adjacent hexane phase. The amount and molecular weight of electrolyte, and solution pH played roles in determining the amount of protein that could be migrated. Low molecular weight polymer under neutral pH conditions, low equilibration time and 1:2 hexane:water ratio favored highest protein separation (~85% dry weight). FTIR and SDS-PAGE studies indicated that the proteins were unfettered and preserved structural integrity after migration from aqueous phase to solvent under the protection of the polymer coating. The results indicate that ionic electrolytes with hydrophobic moieties could be used as molecular transport vehicles to safely separate proteins from a bulk aqueous phase to a totally immiscible solvent phase.

Efforts are continuously being made for exploring various sources of proteins with a need to suffice the demand for nutritional foods with the ever increasing global population. Value added products from algae are slowly gaining momentum in the food and the therapeutic industries for the same reason as algae are considered an excellent source of bio-products. Other than just proteins, algae is also a good source for many other products such as peptides, carbohydrates, lipids, vitamins, pigments, minerals and other valuable trace elements [42]. The protein content in algae can vary from 6 percent (% of dry matter) in *Spirogyra* sp. to as high as 71 percent in *Arthrospira maxima*. But, because of the dilute nature of the microalgae suspensions, 0.3-5 kg/m$^3$ [43, 44], harvesting of these cells and extracting value added products becomes energy and time intensive. Because of this nature, harvesting is considered as a major bottleneck for scaling up the microalgae cultures [45-48]. Techniques that can successfully separate proteins from a complex mixture of cellular biomass in a single step still remains a scientific challenge.

In general, harvesting bio-products from microalgae is currently done in three steps. The original suspension is concentrated up to 2-7% total suspended solids (TSS) by sedimentation, flotation and/or flocculation in first step. This is followed by the thickening step, which further increases the algal concentration in the culture to 15-25% TSS by highly energy intensive processes like filtration and centrifugation [31, 32, 49, 50]. Once the algae have been harvested, the cells are broken down to access the intracellular products of interest like proteins. The cell debris is filtered out to separate water soluble proteins from the junk material. Water soluble proteins are then separated using various techniques like salting-out, precipitation, membrane filtration etc. Aqueous systems resulting from the disintegrated biomass is extremely heterogeneous and needs a lot of processing to separate out the components of interest.

Aqueous two phase separation of proteins has been widely studied because of its biocompatibility, ease of scalability, low toxicity of phase forming chemicals and continuous operation [51]. Recently studies have been conducted on a three phase partitioning (TPP) system where an organic solvent like t-butanol is used to separate proteins from aqueous medium. It has been extensively used to separate various target proteins [52-56]. In a TPP system, with the addition of a salt, proteins precipitate out and form an intermediate later between water and the organic solvent. Ammonium sulphate and organic solvent t-butanol reinforce each other's physicochemical effects, such as ionic strength effects, kosmotrophy, osmotic stresses and exclusion crowding effect to partition the proteins as a midlayer between aqueous and organic phases [56].

Isolating selected proteins from a complex colloidal mixture is quite technically challenging [57]. Separating selected solids or classes of solids from multi-component mixtures is common in bio-processing. Research has also been conducted on use of aqueous-organic two phase systems but because of the low solubility of biomolecules in the organic solvents, it is considered to be less suitable for separation systems [51].

Addressing the solubility issue of proteins in organic solvent can help us achieve a very efficient separation method. It will not only reduce the strain on energy requirement for separating proteins from aqueous suspensions but also help reduce processing time and costs.

In one embodiment, the current invention contemplates a separation technique to selectively separate substrate (i.e. proteins) from an aqueous mixture by migrating it from aqueous phase into an adjacent immiscible (hydrophobic-liquid) phase by using an ionic polyelectrolyte that can transpose the hydrophilicity of the substrate's surface to make it hydrophobic. It is believed that the polyelectrolyte and the substrate may be hydrophilic in their detached (or isolated) states, but become hydrophobic instantaneously when they are interfaced together. This facilitates migration of the hydrophobic groups from an aqueous phase to an immiscible organic solvent phase thereby forming a two phase system (e.g., a biphasic mixture). As described in Example 5, the present results show that under optimum condition of pH, temperature, polyelectrolyte concentration and equilibration time, protein migration of up to 80-85% of its original quantity (dry weight basis) can be achieved.

It is believed that this technique can be easily scaled up and can a good replacement for high energy intensive separation techniques like membrane filtration and centrifugation. Adjusting the polymer concentration, it is possible to avoid mixing of the water-organic phases after the separation is been completed in-turn making the technique extremely robust.

Conclusions:

The migration behavior of egg albumin extract from aqueous phase to hexane solvent phase in the presence of polymeric electrolyte surfactant PolyDADMAC was investigated in Example 5 as an example of one embodiment of the present invention. Studies indicated that the cationic polymer was successfully able to migrate proteins from aqueous phase to an adjacent hexane phase. Although higher times and higher temperatures (between 20 and 40° C.) tended to favor protein migration, this was not statistically significant. The impact of hexane:water ratios, i.e., 2:1, 1:1 and 1:2, on protein migration indicated that maximum protein migration occurred at a hexane:water ratio for 1:2. Studies with low, medium and high molecular weight electrolytes indicated that the amount of the proteins in the water phase decreaseed, i.e., higher migration to solvent phase occurred, with polymeric forms as compared to the monomeric form of the electrolyte. However, when considering polymerific forms, low molecular weight form performed better as compared to high or medium forms. It appears that there is an optimal polyelectrolyte form that is lighter enough to promote upward movement of electrolyte-bound-protein ensemble. Considering acidic, neutral and basic conditions, neutral pH appeared to be the best that promote protein migration. Neutral pH caused the zeta-potential of the final ensembles to reach near zero suggesting effective charge neutralization—that in turn translated to better protein migration. Although higher polymer concentrations in general did not favor particle migration under acidic or basic conditions, higher polymer concentrations did not negatively impact, in fact, favored protein migration under neutral pH conditions. FTIR and SDS-PAGE studies in Example 5 indicated that the proteins were unfettered and preserved structural integrity after migration from aqueous phase to solvent under the protection of the polymer coating. The results indicate that ionic electrolytes with hydrophobic moieties could be used as molecular transport vehicles to protect and separate proteins from a bulk aqueous phase to a totally immiscible solvent phase.

EXAMPLES

The following examples are provided in order to demonstrate and further illustrate certain preferred embodiments and aspects of the present invention and are not to be construed as limiting the scope thereof.

Example 1

Materials and Methods
Microorganism and Culture Condition

*Nannochloropsis oculata* was selected for the investigation. The composition of the cultivation medium comprised a limited amount of nitrogen to provide growth stress to increase the production of oil in the algal cells. Standard cultures were grown in outdoor open pond raceway facilities for a period of 14 days. At the end of the growing phase, algal cells were concentrated by centrifuge from approximately 0.1% to 10% v/v final concentration. The 10% v/v algal concentrate samples were transported and transferred into 1 liter bottles and maintained at 42 degrees C. until used.

Experiments

Characteristics of the process were studied by investigating combinations of the following parameters: Algal surface modifier type, algal surface modifier concentration, solvent-to-broth broth ratio, settling time, and initial algal broth concentration. All tests were conducted in 30 ml glass vials (outer diameter=25 mm and height=95 mm, VWR LLC.) sealed with screw-thread twist top caps. Each tube received stressed algae at an initial culture concentration of 0.1% or 10% v/v. Then the appropriate volume of algal surface modifier (1% or 5% by weight) determined by the mass of algae present in each tube was added. Algal cell surface modification was achieved by three types of industry standard flocculants. Characteristics of each reagent grade flocculant used in this study are provided in Table 3.

TABLE 3

List of Organic Polymers Examined for Solvent Phase Algal Migration

| Polymer Commercial Name | Molecular Weight | Chemical Character | Manufacturer |
| --- | --- | --- | --- |
| FL-5228 Melamine-Formaldehyde | High | Cationic | SNF Inc. Riceboro, GA |
| PDADMAC Poly (Diallyl-dimethylammonium chloride) | Very low | Cationic polyelectrolyte | Sigma-Aldrich |
| ADDAC Poly (Acrylamide-Co-Diallyl dimethylammonium chloride) | Data not available | Cationic polyacrylamide | Sigma-Aldrich |

Note:
Unless otherwise noted, average $M_w$ 400,000-500,000 (high molecular weight), average Mw 100,000-400,000 (medium molecular weight), and average $M_w$ <100,000 (very low molecular weight)

After sealing the vials with screw top caps the contents were vortex mixed at 10,000 rpm for 30 seconds. Next, caps were removed to add the specified volume of chloroform. The amount of chloroform added was determined by the solvent to broth ratio (25% and 75%). More specifically, at S:B ratio 75% for every X ml of algae there will be (30–X) ml of chloroform added to achieve a 75:25 level of S:B ratio. For example, at initial algal broth concentration of 0.1% the solvent:broth ratio by percent 25:75 is converted by volume to 7.5 ml chloroform solvent: 22.5 ml of culture with a concentration of 0.1%. Tubes were sealed again and vigorously shaken manually for 30 seconds, then vortexed 10,000 rpm for two minutes. The end of the two minute mixing marked the beginning of the settling time for the experiments.

Determination of Moisture Content, Dry Solids Content, and Solvent Phase Algal Migration Efficiency After the completion of the settling time, up to 3 ml of sample from the water phase (top layer) and up to 3 ml of the organic solvent phase (bottom layer) were placed in aluminum trays. Samples were placed in the oven at 70 degrees C. for one hour to remove residual solvent. To procure data for wet basis moisture content analysis samples were then placed in the oven at 105 degrees C. until drying was complete. The oven dried samples were allowed to cool in a dessicator after which they were weighed to obtain data for the calculation of the algal biomass dry solids content per unit of volume of medium. The solvent phase algal migration efficiency was evaluated by comparing the remaining algal cell biomass in the water phase (top layer) region after drying with the concentration of algal biomass before solvent phase algal migration treatment.

Example 2

Methodology

*Nannochloropsis oculata* algal samples that have been subjected to nitrogen deprivation for increasing lipid content were obtained from algal culturing facility in Pecos, Tex. Lipid content of the samples is around 12% (w/w dry basis). These samples were concentrated to 22% TSS (Total Suspended Solids) using centrifugation, prior to shipping using centrifugation. Upon arrival, samples were refrigerated at 18° C. until used.

PolyDADMAC (Sigma Aldrich) with three different molecular weights (High: 400,000-500,000, Medium: 100,000-200,000 and Low: <100,000) were used as the surfactant. All surfactant samples were diluted to 20 g/l solid content using deionized water for ease of transferring and to increase the measurement accuracy.

Algal samples were diluted to 10% TSS using deionized water before the experiment. 10 ml of the 10% TSS algal sample was transferred to a 30 ml screw cap vial and 500 ml surfactant was added to the algal sample. After vortexing it for 1 min at 10,000 rpm, 10 ml of the solvent; Hexane, chloroform or dichloromethane; was added. Mixture was vortexed for 1 min at 10,000 rpm and left to settle for 1 h or 24 h time period. During this time period mixture separates in to two layers: solvent phase and aqueous phase. For experiments with hexane, aqueous phase separates to the bottom while for experiments with chloroform or dichloromethane, aqueous phase separates to the top.

Aqueous layer was removed using a pipette and the volume recorded ($V_{aq}$). After vortexing the aqueous layer for 10 s, 1 ml of the layer ($V_{aq,0}$) was transferred to a pre-weighed, pre-washed aluminums dish. If the aqueous layer volume was very small, removing aqueous layer from solvent phase without disturbing the interface becomes difficult; therefore, only a portion of the aqueous layer ($V_{aq,0}$) was used for dry weigh measurement (to ensure that the aqueous portion does not include any solvent). The remainder of the aqueous layer was separately siphoned in to a 1 ml graduated pipette and allowed to separate (in the pipette). Then the amount of aqueous portion was noted and summed with $V_{aq,0}$ to obtain $V_{aq}$ value. Then, aluminum dish was dried in an oven until constant weight to obtain the residue weight. The same procedure was followed for the solvent phase.

Figure 11:
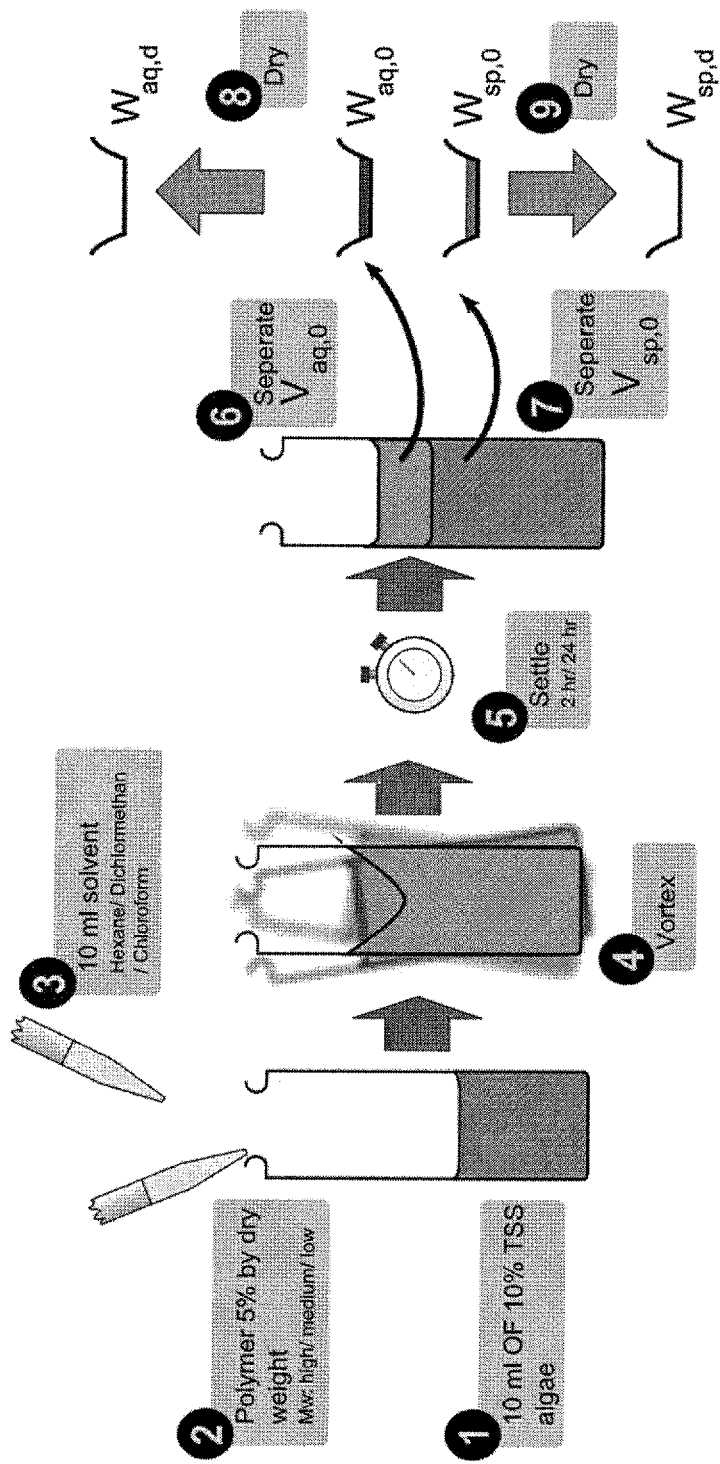
FIG. 11 shows an illustrative summary of one embodiment of the methodology of the current invention.

Graphic summary of the experimental procedure is illustrated in FIG. 11.

TSS of the aqueous layer, Solid content of aqueous layer, TSS of solvent layer, and the solids content of solvent layer was calculated using equations 1 to 5.

Transfer efficiency of solids from aqueous medium to solvent phase was calculated using equation 5.

TSS of the aqueous layer $TSS_{aq}$ can be calculated using equation (1)

$$TSS_{aq} = W_{aq,d}/W_{aq,0} \qquad \text{Equation 1}$$

where $W_{aq,0}$ is the weight of $V_{aq,0}$ and $W_{aq,d}$ is the dry weight of that sample Solid content in aqueous layer ($S_{aq}$) can be calculated using equation (2)

$$S_{aq} = W_{aq,d} \times V_{aq}/V_{aq,0} \qquad \text{Equation 2}$$

TSS of the solvent layer $TSS_{sp}$ can be calculated using equation (3)

$$TSS_{sp} = W_{sp,d}/W_{sp,0} \qquad \text{Equation 3}$$

where $W_{sp,0}$ is weight of the solvent volume $V_{sp,0}$ removed for TSS measurement and $W_{sp,d}$ is the dry weight of that volume.

Solid content in solvent layer can be calculated using equation (4)

$$S_{sp} = W_{sp,d} \times V_{sp}/V_{sp,0} \qquad \text{Equation 4}$$

$V_{sp}$ was derived from equation (5)

$$V_{sp} = V_T - V_{ap} \qquad \text{Equation 5}$$

where $V_T$ is the total volume of the mixture, calculated by adding the volumes of algal broth and solvent volumes.

Example 3

Methods

1. Required amount of polymeric/oligomeric/monomeric cationic electrolytes with hydrophobic ligands/residues (such as poly/monomeric DADMAC) are added to algal water and mixed vigorously using a vortex mixer.
2. The water-immiscible solvent is added to above sample and mixed thoroughly.
3. The system is allowed to stand undisturbed to promote separation. The electrolyte-bound algae are observed to migrate from aqueous phase to the immiscible solvent phase.
4. After the system reaches equilibrium, the two phases are separated carefully to avoid mixing (of the phases). The water phase is carefully separated from the hexane phase using a micropipette, syringe or a separatory funnel and used for gravimetric analysis.
5. Dilution of the polymer first in water and adding to algal suspension is done to ensure polymer dispersion to improve surface coverage of polymer on algae.
6. Adequate surface coverage of polymer can be ensured by changing the electrolyte type and molecular weight (chain length, i.e., low, medium and high molecular weight polymer and monomer).

7. Hydrophobicity of the surface of the electrolyte-bound ensemble can be modulated by changing the hydrophobic ligand/residue(s) of the electrolyte.
8. The type and molecular weight of electrolyte could be varied to form fissures in the algal surface promoting internal water removal.
9. For separating any other material other than algae (e.g., proteins, lipids, carbohydrates, pigments) from a biological matrix, an analogous process consisting of anionic or cationic electrolytes (depending on the surface potential of the material to be separated) is used.

Example 4

Methodology:
1. Protein solution (4% w/w) was prepared using DI water.
2. Polymer and monomer solution of 1% w/w and 5% w/w of protein was prepared by diluting it to the same volume of the protein solution. This ensured good dispersion of the surface modifier in the water.
3. The polymer solution was added to the protein solution and mixed thoroughly to make sure that the surface modifier was bound to the proteins. The total volume of water was 10 ml and the protein content was then 2% w/w.
4. 10 ml of hexane was added to the system and the water-hexane system was vortexed for 1 minute at maximum speed.
5. The system was kept undisturbed to allow the migration of proteins from aqueous phase to hexane phase.
6. Samples were collected from water and hexane for further analysis.

Figure 16:
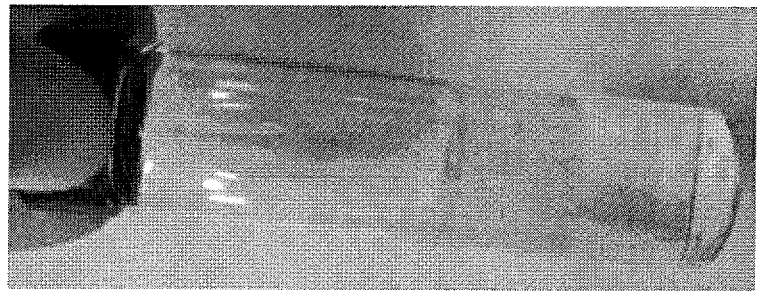
FIG. 16 shows a model protein completely migrated from clear aqueous phase to an adjacent solvent (and forming an easy to separate gel) after interacting with ionic electrolytes.

Results:
Migration behavior of albumin using cationic electrolyte from aqueous to organic (e.g. hexane) phase was investigated. FIG. 16 depicts images of protein separation of which migrated protein appears at the top as an easy to separate gel and protein-depleted aqueous phase at the bottom.

Table 4 shows the results from the preliminary studies conducted. Results indicated that the polymeric form, poly-DADMAC has a more positive impact on the amount of albumin migration from aqueous phase to an adjacent water-immiscible solvent phase as compared to its monomer, DADMAC. Studies also show that when the polymer used at higher concentration (5% w/w), the amount of albumin migrating from water to hexane increased as compared to the lower concentration (1% w/w). Effect of temperature was also studied and it was observed that the temperature variation (between 4 and 20° C.) did not have any significant impact on the amount of albumin migrated.

TABLE 4

| SM | Concentration (w/w %) | pH | Time (hr) | Temperature (° C.) | Corrected Weight (g) | Yield (% w/w) |
|---|---|---|---|---|---|---|
| Polymer | 1 | 7 | 3 | 4 | 0.062 | 31.08 |
| Monomer | 1 | 7 | 3 | 20 | 0.06 | 29.76 |
| Polymer | 1 | 7 | 3 | 20 | 0.066 | 32.911 |
| Monomer | 1 | 7 | 3 | 4 | 0.056 | 28.21 |
| Polymer | 5 | 7 | 3 | 20 | 0.066 | 33.07 |
| Monomer | 5 | 7 | 3 | 4 | 0.052 | 25.79 |
| Polymer | 5 | 7 | 3 | 4 | 0.071 | 35.74 |
| Monomer | 5 | 7 | 3 | 20 | 0.056 | 28.07 |

Example 5

Material and Methods
Egg albumin extract and hexane were purchased from VWR® and poly-(dialyldimethylammonium chloride (average $M_W$ 200,000-350,000 (medium molecular weight), 20 wt. % in $H_2O$) was purchased from Sigma Aldrich®.

Figure 17:
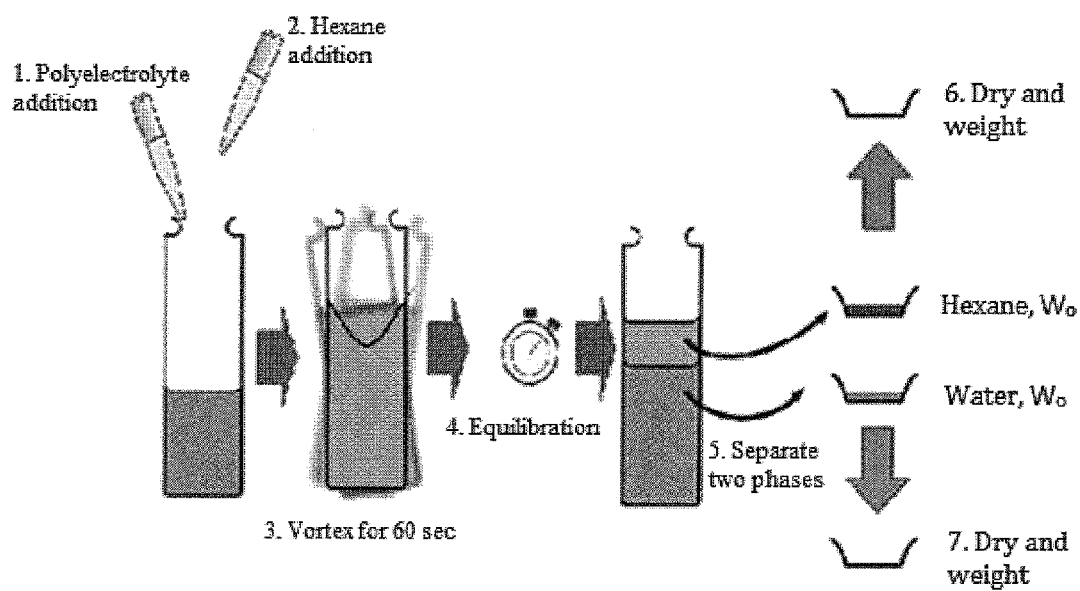
FIG. 17 shows a schematic of the protein migration process and the analytical procedure (Note: $W_0$, Water—Weight of particles in water phase. W0, Hexane—Weight of particles in Hexane phase) Measuring Zeta potential of the egg albumin suspension: Zeta potential is the surface charge a molecule carries. The zeta potential of the egg albumin was measured using Beckman Coulter (Delsa Nano C) Zeta Sizer. The zeta potential of the proteins was measured using a flow cell. The surface charge was measured for proteins at different system pH before subjecting to the migration process. Water samples were collected and again analyzed for zeta potential after the two-phase separation occurred to evaluate the effect of the polymer addition on the zeta potential of the proteins remaining in the water system.

Quantification of Proteins:
Once the polyelectrolyte gets adsorbed onto the protein, the polyelectrolyte-attached-protein transposes the hydrophilicity of the protein and makes the protein-polymer ensemble hydrophobic. Addition of hexane to this suspension results in the migration of the proteins to the top phase i.e. the hexane. Once the migration was completed, samples were collected from the aqueous phase and analyzed on thermogravimetric analysis, TGA (Q50, TA Instruments) to quantify the amount of proteins remaining in the aqueous phase. Low the amount of proteins in the bottom phase corresponded to higher extraction efficiency. of the polymer onto the proteins, the mixture was vortexed for 30 seconds at high speed. Hexane was added to the aqueous suspension and the water-hexane system was again vortexed for 1 minute at maximum speed. The system was kept undisturbed for the phases to separate. Samples were drawn from both the hexane and aqueous phases and analyzed on the Thermo-Gravimetric Analyzer (TGA). The amount of protein in the original suspension was used to calculate the amount left in the water phase. As TGA results of the hexane phase showed large variations from sample to sample, the amount of proteins remaining in water phase were used to calculate protein migration (FIG. 17).

Experimental Design:
Table 5 depicts the independent variables and its corresponding levels chosen for detailed parametric studies of the system.

TABLE 5

Factors and levels used in the parametric study.

| Factor | Level(s) |
|---|---|
| Type of Electrolyte Surface Modifier | PolyDADMAC |
| Electrolyte Surface Modifier (SM) concentration (w/w %) | 0.5-3 (at 0.5% intervals) |
| Temperature (° C.) | 20° C., 30° C. and 40° C. (room) |
| pH | 6, 7, and 8 |
| Equilibration time (min) | 20, 30 and 40 |
| Solvent: water ratio (v/v) | 1:1, 1:2 and 2:1 |

Figure 18:
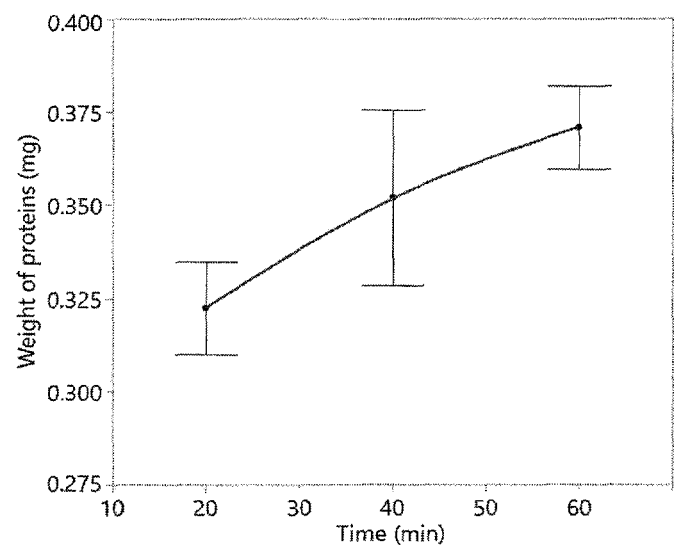
FIG. 18 shows the effect of equilibration time on albumin migration from aqueous phase to solvent phase.

Results and Discussion:
Effect of Time:
FIG. 18 shows the impact of different equilibration times on the amount of albumin migration from aqueous phase to the hexane phase. It is evident that longer equilibration times favored more proteins migration. Nevertheless, the results were not statistically significant. To remove discrepancies associated, equilibration time was kept constant during remaining experiments at 60 minutes.

Figure 19:
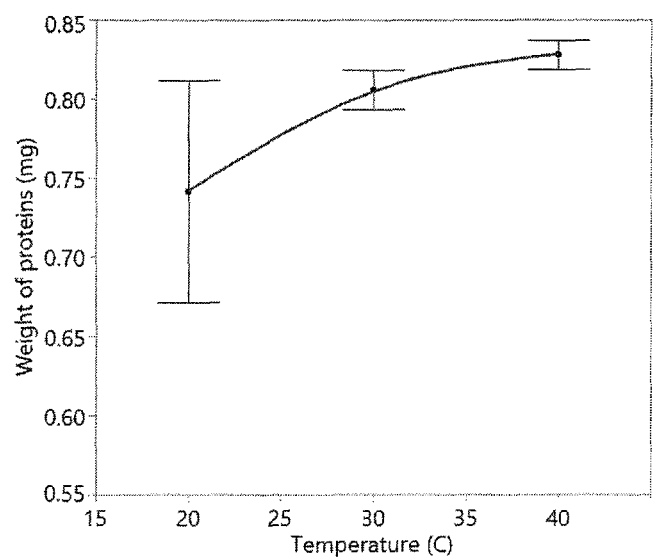
FIG. 19 shows the effect of temperature on protein migration from aqueous phase to solvent phase.

FIG. 19 shows the effect of temperature on particle migration from aqueous phase to hexane phase with polymer addition. It could be noted that higher temperatures tended to favor migration; however, the impact was not statistically significant. Extraction efficiencies of proteins in two phase systems are reported to increase with the increase in temperature because of the endothermic nature of the extraction process [58].

Figure 20:
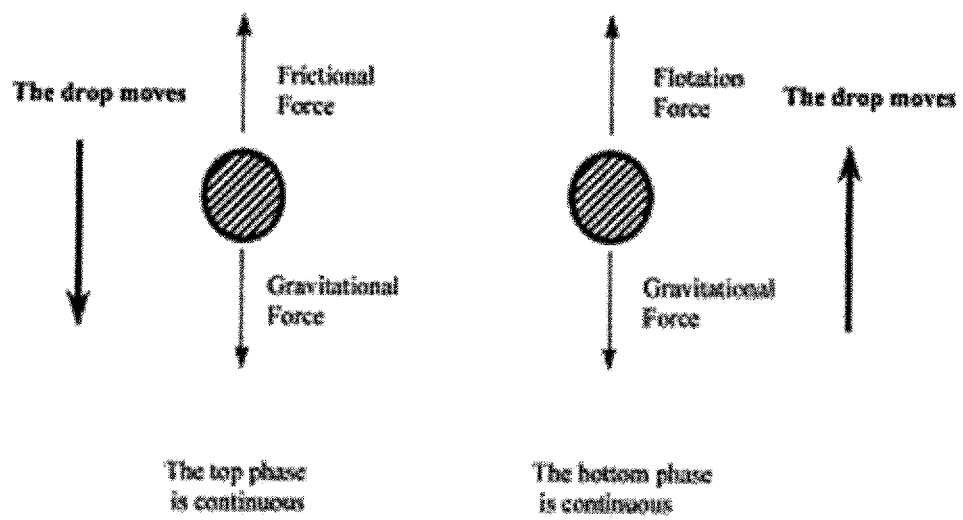
FIG. 20 shows a diagram showing the different forces acting on a drop depending on which phase is continuous [2].

Gravitational, flotational and frictional forces act on a drop during coalescence [2]. The migration of proteins will depend on the balance of these forces. In two phase systems, the flotation forces will determine the behavior of the drops [59]. FIG. 20 shows the different forces acing on a drop depending on which phase is continuous. The viscosity of water is almost thrice as compared to hexane at room temperature. For the proteins to migrate from aqueous phase to hexane phase against the gravitational force, aqueous phase offers the most resistance. With the increase in temperature, the viscosity of water reduces significantly. This reduces the frictional forces between water molecules and the polyelectrolyte bound proteins resulting in the increase in the migration efficiency of proteins.

Figure 21:
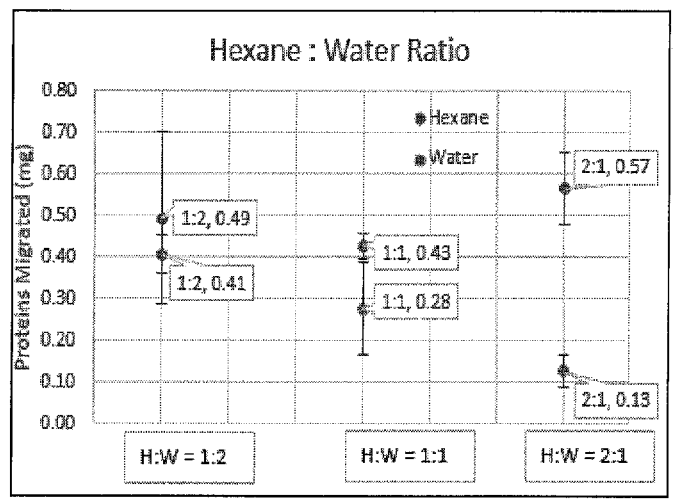
FIG. 21 shows solids migration as a function of hexane (H) to water (W) ratio.
Figure 22:
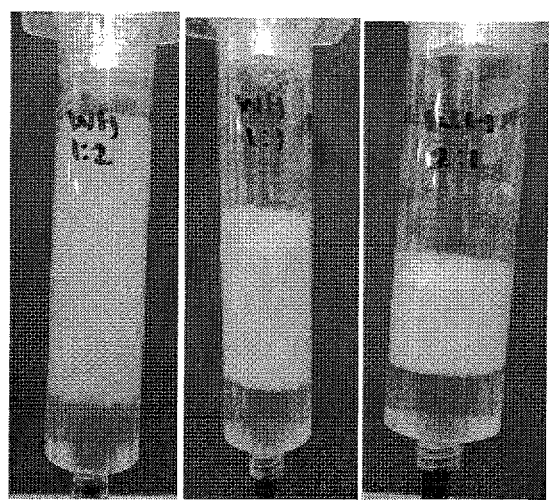
FIG. 22 shows solids migration in various ratios of hexane (H) to water (W) ratio.

Effect of Water to Hexane Ratio:

To test whether water to hexane ratio would be a limiting factor for the migration of particles, a study was conducted at three different hexane:water ratios, i.e., 2:1, 1:1 and 1:2, while keeping pH, time, temperature, polyelectrolyte concentration constant. FIG. 21 and FIG. 22 shows that maximum protein migration occurred at a hexane:water ratio for 1:2. For the constant equilibration time, the rate of migration of proteins depends on the relative size of the two phases. Larger the top phase, slower is the phase separation [2]. However during further studies, the hexane:water ratio was kept at 1:1 considering the fact that for practical purposes, handling large amounts of solvents were disadvantageous.

Figure 23:
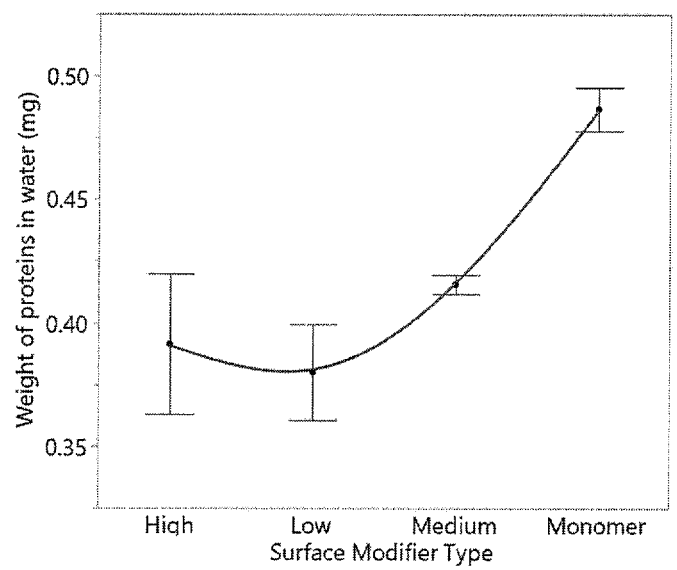
FIG. 23 shows the effect of surface modifier type on the migration system.
Figure 24:
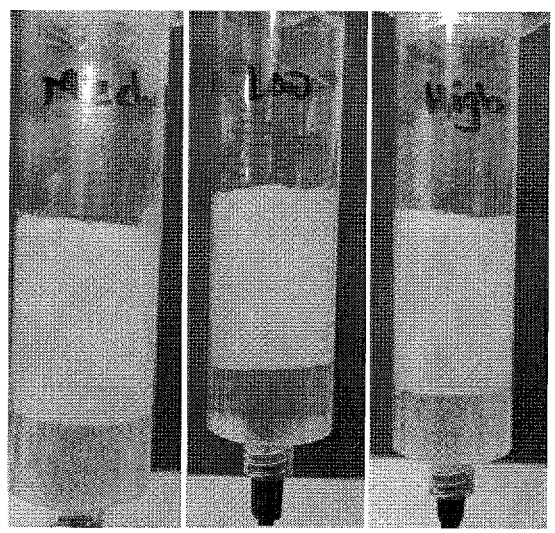
FIG. 24 shows that the water phase tends to become milky with the increase in the molecular weight of the polymer.

Effect of Polyelectrolyte Type on the Protein Migration:

Effect of different electrolyte molecular weight on the protein migration was studied. Low, medium and high PolyDADMAC ranging from <100,000, 200,000-350,000 and 400,00-500,000 units along with the monomeric form (DADMAC) were used. Results indicate that the amount of the proteins in the water phase decreased, i.e., higher migration to solvent phase, with polymeric forms as compared to monomeric form of the electrolyte. This may be as a result of formation of flocs that assist migration. However, when considering polymerific forms, low molecular weight form performed better as compared to high or medium forms. It appears that there is an optimal polyelerctrolyte form that is lighter enough to promote upward movement of electrolyte-bound-protein ensemble. In retrospect, higher molecular weight causes the ensemble to get heavier increasing the resistance for the movement of proteins from water phase to the upper hexane phase. FIG. 23 shows the effect of surface modifier type on the migration system. FIG. 24 shows that the water phase tends to become milky with the increase in the molecular weight of the polymer.

Effect of Polyelectrolyte Concentration and pH on Ensemble Migration:

Zeta potential of particles changes as a function of the system pH it is suspended in. From the previous work done with carboxyl functionalized cellulose beads, it is evident that pH plays a vital role in deciding the concentration of the polyelectrolyte to be added for maximum ensemble migration to occur. ANOVA output suggests an interdependent relationship of the two parameters on the migration process. The zeta potential before polymer additions was measured for the three pH levels and was found to be −3.72 mV, −6.58 mV and −25.1 mV for pH 6, 7, and 8 respectively (FIG. 25A). A further analysis (FIG. 25B) [3] indicates that this system lies in the region marked by a red oval in the generalized pH vs. Zeta-potential curve alluding that the system is well dispersed and a reduction of pH would force the system to arrive at its isoelectric point—which also would lead to floc formation (indicating the possibility of better particle separation/migration from aqueous phase given adequate hydrophobicity is attained). The study performed showed the cross interaction between system pH (varied between 6, 7 and 8) and polyelectrolyte concentration (varied from 0.5 to 3% w/w at 0.5% intervals) to be significant.

FIG. 25C and FIG. 25D clearly suggests that under neutral pH conditions, the amount of proteins migrating to hexane phase is optimum. Low net negative surface charge of proteins before polymer addition adsorbs only a low amount of polymer to the protein making the ensemble hydrophobic as well as light enough to move against the gravity with minimum resistance. In contrast, acidic conditions make proteins even less net negative (as compared to neutral pH); therefore, attracting lower amounts of polymer essentially making the ensemble "less" hydrophobic in turn reducing the amount of ensemble migration as compared to neutral conditions. When the system pH is in basic, the highly negative surface charge attracts higher amounts of cationic polymer making the protein-surfactant ensemble heavy resulting in increased resistance for particles to move upward against gravity.

After the two phases were separated, the zeta potential of the ensembles suspended in water phase was measured. Results clearly suggest that the polyelectrolyte addition causes zeta potential to approach near zero irrespective of the initial surface charge suggesting charge neutralization (FIG. 25D).

To understand the impact of each of the variables more clearly, protein migration as a function of different polymer concentration, pH and zeta potential is depicted in FIG. 26A-C.

It could be noted from FIG. 26A that as polymer concentrations increases, the zeta-potential of the polymer-bound ensemble tends to increase. At lower polymer concentrations, the final zeta-potential tends to stay near zero suggesting charge neutralization that in turn promotes protein migration. However, as the polymer concentrations increases, the system becomes charged again (i.e., positively), adversely impacting protein migration. FIG. 26B further clarifies the positive impact of lower polymer concentrations on protein migration (i.e., lower retention of proteins in water signifies higher migration).

The impact of pH on zeta potential (after polymer addition) and protein migration is depicted in FIG. 26C. At pH 6, it could be noted that the zeta potential of polymer-bound ensembles are still slightly negative—retaining higher amounts of proteins in water. However, at neutral pH, the zeta potential reached near zero suggesting the system reached charge neutralization that in turn translated to comparatively lower protein retention (and thus higher migration) as compared to acidic conditions. Under basic conditions, the zeta potential of polymer-bound ensembles regressed to negative (potential) negating charge neutralization (and thus lowering polymer binding) that translated to more protein retention. Under acidic and basic conditions, it appears that addition of extraneous $H^+$ or $OH^-$ ions causes zwitterionic proteins to preferentially interact with these ions isolating the polymer interacting with the proteins.

Above observations clearly suggests that along with the change in Zeta-potential (as a function of pH variation) presence of free H+ or OH− ions in the system significantly impacts the migration efficacy of the proteins. So, it is evident that there is an optimal combination of conditions that promote electrolyte binding, floc formation and mobilization; and in this system, the most effective conditions to obtain the desired output seems are 3.0% polyelectrolyte at pH7.

Figures 27A, 27B:
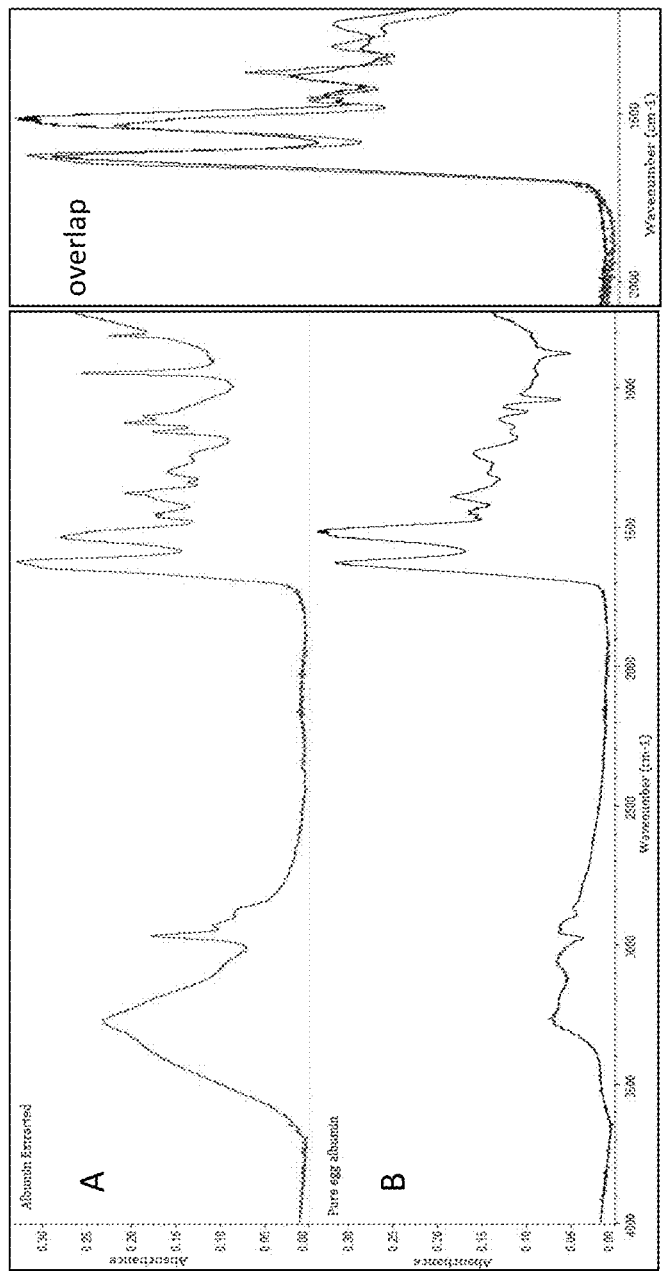
FIGS. 27A&B shows FTIR Spectra of (FIG. 27A) pure egg albumin and (FIG. 27B) albumin after extraction and an overlap of the two.

Examination of the Protein Conformations Before and after Migration:

To investigate the protein conformations before and after migration from aqueous to solvent phase, FTIR spectra of albumin were studied. FIG. 27A shows the FTIR spectra of pure egg albumin extract and FIG. 27B shows that of the proteins from hexane phase after the migration process was completed. As seen from the FIG. 27B, the amide 1 bond (1652 $cm^{-1}$) and amide 11 bond (1520 $cm^{-1}$) of the protein were identified in the spectra. The two peaks were retained in the FTIR spectra of the extracted proteins; clearly indicating successful migration. The large peak in the extracted proteins spectra (3200-3550 $cm^{-1}$) corresponds to the O—H bond stretching from the polyelectrolyte. It also confirms the binding of the polyelectrolyte to the proteins. The amide 11 peak is slightly shifted in the positive direction (1538 $cm^{-1}$) of the spectra which can be due to the physisorption of the polymer with the proteins. Cationic surfactants are generally not as potent as anionic surfactants; in fact in some cases cationic surfactants manage to preserve protein activity for longer durations compared to native protein in the absence of surfactant additives [60]. The coexistence of protein and small amounts of ionic surfactant is believed to rely on specific interactions with the native state; thus surfactants assuming the role of a conventional ligand that stabilizes proteins and protects the helical structures [61]. Thus, it could be concluded from the FTIR analysis and previous studies that the aqueous-organic two-phase protein separation system provides a gentle environment preserving the structural integrity of proteins.

Figure 28:
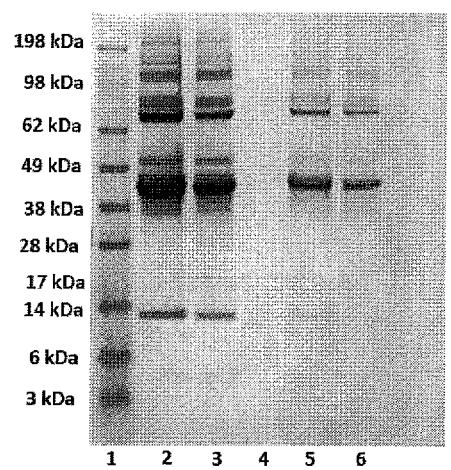
FIG. 28 shows an SDS-PAGE of extracted proteins using Separation of Proteins using Ionic Nanomaterials (S.P.I.N.). Lane: 1) molecular weight marker; 2) Albumin sample diluted 10×; 3) albumin sample 20×; 4) Blank; 5) Polymer-albumin 10×; 6) Polymer-albumin 20×.

SDS-Page Analysis:

SDS-PAGE analysis of protein extracted using 3% (w/w) polymer, pure egg albumin extract and molecular weight marker is represented in the FIGS. 27A&B). It was observed that the molecular weight of the proteins separated using aqueous-organic two phase system matched with the pure egg albumin suspension indicating that the structural integrity of the protein is preserved even after transferring into organic phase. FIG. 28 shows SDS-PAGE of extracted proteins using S.P.I.N. Lane: 1) molecular weight marker; 2) Albumin sample diluted 10×; 3) albumin sample 20×; 4) Blank; 5) Polymer-albumin 10×; 6) Polymer-albumin 20×.

Figure 29A:
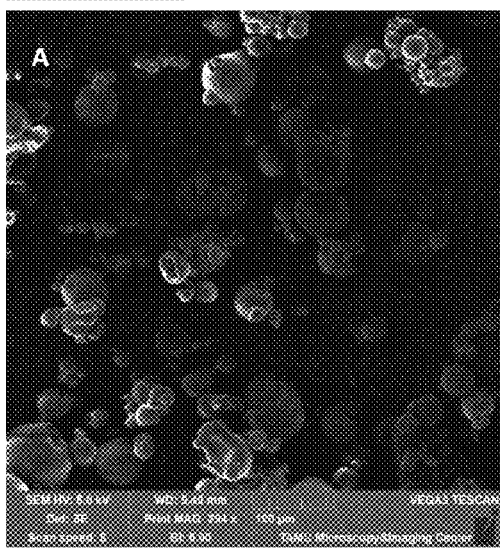
FIGS. 29A&B shows scanning electron microscopy images of protein and protein-polymer complex.
Figure 29B:
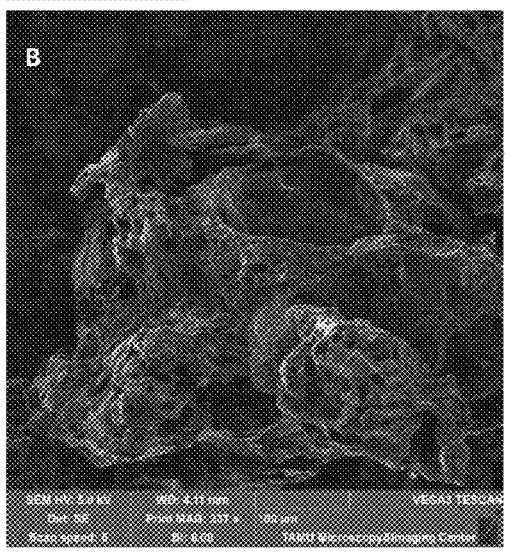
FIG. 29B shows an image of a single protein unit (944×).

SEM Analysis:

Scanning electron microscope (SEM) images of the protein and protein-polymer complex are shown in FIGS. 29A&B. It is clear that the polymer is well dispersed in water in its native state (FIG. 29A) and once mixed with protein, forms clear flocs (FIG. 29B) forming a blanket over protein aggregates-helping migration.

Thus, specific compositions and methods of moisture displacement and simultaneous migration of surface-functionalized algae from water to an extraction solvent using ionic polyelectrolytes have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Kanda, H. and Li, P. (2011) "Simple Extraction Method of Green Crude from Natural Blue-Green Microalgae by Dimethyl Ether," *Fuel* 90(3), 1264-1266.
2. Salamanca, M. H. et al. (1998) "On the Kinetics of Phase Separation in Aqueous Two-Phase Systems," *Journal of Chromatography B: Biomedical Sciences and Applications* 711(1), 319-329.
3. Fairhurst, D. (2013) "An Overview of the Zeta Potential Part 3: Uses and Applications," *American Pharmaceutical Review*.
4. Fleischer, D. et al. "Systems and Methods for Extracting Lipids from and Dehydrating Wet Algal Biomass," United States Patent Application Publication Number US 2010-0261922 A1, application Ser. No. 12/610,134, (published Oct. 14, 2010).
5. Downey, R. "Solubilization of Algae and Algal Materials," United States Patent Application Publication Number US 2010-0068772 A1, application Ser. No. 12/584,300, (published Mar. 18, 2010).
6. Oyler, J. R. "Process of Producing Oil from Algae Using Biological Rupturing," United States Patent Application Publication Number US 2010-0304452 A1, application Ser. No. 12/790,588, (published Dec. 2, 2010).
7. Hoeksema, S. D. "Two Phase Extraction of Oil from Biomass," U.S. Pat. No. 6,166,231, application Ser. No. 09/210,598, (issued Dec. 26, 2000).
8. Bijl, H. L. and Schaap, A. "Isolation of Microbial Oils," U.S. Pat. No. 7,431,952, application Ser. No. 10/343,861, (issued Oct. 7, 2008).
9. Whittaker, T. et al. "Dewatering Process," U.S. Pat. No. 7,749,392, application Ser. No. 10/591,777, (issued Jul. 6, 2010).
10. Divakaran, R. and Pillai, V. N. S. (2002) "Flocculation of Algae Using Chitosan," *J. Appl. Phycol.* 14(5), 419-422.
11. Buelna, G. et al. (1990) "Evaluation of Various Flocculants for the Recovery of Algal Biomass Grown on Pig-Waste," *Biological Wastes* 31(3), 211-222.
12. Chisti, Y. (2007) "Biodiesel from Microalgae," *Biotechnol. Adv.* 25(3), 294-306.
13. Spolaore, P. et al. (2006) "Commercial Applications of Microalgae," *J. Biosci. Bioeng.* 101(2), 87-96.
14. Golueke, C. G. and Oswald, W. J. (1965) "Harvesting and Processing Sewage-Grown Planktonic Algae," *J. Water Pollut. Control Fed.* 37(4), 471-498.
15. Ehimen, E. A. et al. (2010) "Variables Affecting the in Situ Transesterification of Microalgae Lipids," *Fuel* 89(3), 677-684.
16. Griffiths, M. J. et al. (2010) "Selection of Direct Transesterification as the Preferred Method for Assay of Fatty Acid Content of Microalgae," *Lipids* 45(11), 1053-1060.
17. Dejoye Tanzi, C. et al. (2013) "New Procedure for Extraction of Algal Lipids from Wet Biomass: A Green Clean and Scalable Process," *Bioresour. Technol.* 134, 271-275.
18. Samarasinghe, N. et al. (2012) "Algal Cell Rupture Using High Pressure Homogenization as a Prelude to Oil Extraction," *Renewable Energy* 48, 300-308.

19. Buckwalter, P. et al. (2013) "Dewatering Microalgae by Forward Osmosis," *Desalination* 312, 19-22.
20. O'Connell, D. et al. (2012) "Life Cycle Assessment of Dewatering Routes for Algae Derived Biodiesel Processes," *Clean Technol. Environ. Policy*, 1-11.
21. Samarasinghe, N. et al. (2012) "Effect of High Pressure Homogenization on Aqueous Phase Solvent Extraction of Lipids from Nannochloris Oculata Microalgae," *J. Energy Nat. Resour.* 1(1), 7.
22. Molina Grima, E. et al. (2003) "Recovery of Microalgal Biomass and Metabolites: Process Options and Economics," *Biotechnol. Adv.* 20(7-8), 491-515.
23. Lardon, L. et al. (2009) "Life-Cycle Assessment of Biodiesel Production from Microalgae," *Environ. Sci. Technol.* 43(17), 6475-6481.
24. Brune, D. E. et al. (2008) "Algal Production and Harvest for Food, Feed, and Biofuels," in 2008 *Microalgae Biomass Summit*, Algal Biomass Organization, Seattle, Wash.
25. Chiu, S.-Y. et al. (2009) "Lipid Accumulation and Co2 Utilization of *Nannochloropsis Oculata* in Response to Co2 Aeration," *Bioresour. Technol.* 100(2), 833-838.
26. Zittelli, G. C. et al. (1999) "Production of Eicosapentaenoic Acid by *Nannochloropsis* Sp. Cultures in Outdoor Tubular Photobioreactors,"*J. Biotechnol.* 70, 299-312.
27. Harun, R. et al. (2010) "Bioprocess Engineering of Microalgae to Produce a Variety of Consumer Products," *Renewable and Sustainable Energy Reviews* 14, 1037-1047.
28. Demirbas, A. (2010) "Use of Algae as Biofuel Sources," *Energy Conversion and Management* 51(12), 2738-2749.
29. Sheehan, J. et al. (1998) "A Look Back at the US Department of Energy's Aquatic Species Program—Biodiesel from Algae (Nrel/Tp-580-24190)," (National Renewable Energy Laboratory (NREL), Ed.), US DOE, Golden, Colo.
30. U.S. DOE. (2010) "National Algal Biofuels Technology Roadmap," (Energy, U. S. D. o., Ed.), Office of Energy Efficiency and Renewable Energy, Biomass Program.
31. Chen, C.-Y. et al. (2011) "Cultivation, Photobioreactor Design and Harvesting of Microalgae for Biodiesel Production: A Critical Review," *Bioresour. Technol.* 102(1), 71-81.
32. Uduman, N. et al. (2010) "Dewatering of Microalgal Cultures: A Major Bottleneck to Algae-Based Fuels," *Journal of renewable and sustainable energy* 2(1), 012701.
33. Wijffels, R. H. et al. (2010) "Microalgae for the Production of Bulk Chemicals and Biofuels," *Biofuels, Bioproducts and Biorefining* 4(3), 287-295.
34. Davis, R. et al. (2011) "Techno-Economic Analysis of Autotrophic Microalgae for Fuel Production," *Applied Energy* 88(10), 3524-3531.
35. Harith, Z. T. Y., F. M. et al. (2009) "Effect of Different Flocculants on the Flocculation Performance of Microalgae, Chaetoceros Calcitrans, Cells," *Afr. J. Biotechnol.* 8(21), 5971-5978.
36. Sim, T. et al. (1988) "Comparison of Centrifugation, Dissolved Air Flotation and Drum Filtration Techniques for Harvesting Sewage-Grown Algae," *Biomass* 16, 51-62.
37. Shelef, G. et al. (1984) "Microalgae Harvesting and Processing: A Literature Review," p Medium: ED; Size: Pages: 70.
38. Yuan, W. et al. (2009) "Microalgae Mass Production Methods," *Transactions of the ASABE* 52(4), 1275-1287.
39. Molina, E. et al. (2001) "Tubular Photobioreactor Design for Algal Cultures," *J. Biotechnol.* 92(2), 113-131.
40. Henderson, R. K. et al. (2010) "The Impact of Differing Cell and Algogenic Organic Matter (Aom) Characteristics on the Coagulation and Flotation of Algae," *Water Res* 44(12), 3617-3624.
41. Klitzing, R. v. et al. (2002) "Structuring of Poly(Dadmac) Chains in Aqueous Media: A Comparison between Bulk and Free-Standing Film Measurements," *Phys. Chem. Chem. Phys.* 4(10), 1907-1914.
42. Becker, E. W. (2007) "Micro-Algae as a Source of Protein," *Biotechnol. Adv.* 25(2), 207-210.
43. Gouveia, L. (2011) "Microalgae as a Feedstock for Biofuels," in *Microalgae as a Feedstock for Biofuels*, pp 1-69, Springer.
44. Li, Q. et all. (2008) "Perspectives of Microbial Oils for Biodiesel Production," *Appl. Microbiol. Biotechnol.* 80(5), 749-756.
45. Cooney, M. (2013) "Case Studies of Separation in Biorefineries—Extraction of Algae Oil from Microalgae," *Separation and Purification Technologies in Biorefineries*, 533-554.
46. Coward, T. et al. (2013) "Development of a Foam Flotation System for Harvesting Microalgae Biomass," *Algal Research* 2(2), 135-144.
47. Delrue, F. et al. (2012) "An Economic, Sustainability, and Energetic Model of Biodiesel Production from Microalgae," *Bioresour. Technol.* 111, 191-200.
48. Grima, E. M. et al. (2003) "Recovery of Microalgal Biomass and Metabolites: Process Options and Economics," *Biotechnol. Adv.* 20(7), 491-515.
49. Brennan, L. and Owende, P. (2010) "Biofuels from Microalgae—a Review of Technologies for Production, Processing, and Extractions of Biofuels and Co-Products," *Renewable and sustainable energy reviews* 14(2), 557-577.
50. Pragya, N. et al. (2013) "A Review on Harvesting, Oil Extraction and Biofuels Production Technologies from Microalgae," *Renewable and Sustainable Energy Reviews* 24, 159-171.
51. Asenjo, J. A. and Andrews, B. A. (2011) "Aqueous Two-Phase Systems for Protein Separation: A Perspective," *J. Chromatogr. A* 1218(49), 8826-8835.
52. Akardere, E. et al. (2010) "Three-Phase Partitioning of Invertase from Baker's Yeast," *Sep. Purif. Technol.* 72(3), 335-339.
53. Mondal, K. et al. (2006) "Emerging Options in Protein Bioseparation," in *Biotechnology Annual Review* (El-Gewely, M. R., Ed.), pp 1-29, Elsevier.
54. Wati, R. K. et al. (2009) "Three-Phase Partitioning of Trypsin Inhibitor from Legume Seeds," *Process Biochem.* 44(12), 1307-1314.
55. Dogan, N. and Tari, C. (2008) "Characterization of Three-Phase Partitioned Exo-Polygalacturonase from *Aspergillus Sojae* with Unique Properties," *Biochem. Eng. J.* 39(1), 43-50.
56. Dennison, C. and Lovrien, R. (1997) "Three Phase Partitioning: Concentration and Purification of Proteins," *Protein Expr. Purif.* 11(2), 149-161.
57. Richard, T. L. (2010) "Challenges in Scaling up Biofuels Infrastructure," *Science* 329(5993), 793-796.
58. Pei, Y. et al. (2009) "Ionic Liquid-Based Aqueous Two-Phase Extraction of Selected Proteins," *Sep. Purif. Technol.* 64(3), 288-295.
59. Asenjo, J. A. and Andrews, B. A. (2012) "Aqueous Two-Phase Systems for Protein Separation: Phase Separation and Applications," *J. Chromatogr. A* 1238, 1-10.

60. Marcozzi, G. et al. (1998) "Effects of Surfactants on the Stabilization of the Bovine Lactoperoxidase Activity," *Biotechnol. Frog.* 14(4), 653-656.
61. Moriyama, Y. and Takeda, K. (2005) "Protective Effects of Small Amounts of Bis (2-Ethylhexyl) Sulfosuccinate on the Helical Structures of Human and Bovine Serum Albumins in Their Thermal Denaturations," *Langmuir* 21(12), 5524-5528.

We claim:

1. A method for the extraction of algal oil comprising:
   a) providing:
      i) algae cells comprising algal oil and a hydrophilic cell surface;
      ii) an amphiphilic agent capable of converting said hydrophilic cell surface to a hydrophobic cell surface, wherein said amphiphilic agent is selected from the group consisting of: Poly(diallyldimethylammonium chloride), Poly(sodium 4-styrenesulfonate), Poly(3-(1-Pyridinio)-1-propanesulfonate), a monomeric form of at least one of the group consisting of diallyldimethylammonium chloride, sodium 4-styrenesulfonate, and 3-(1-Pyridinio)-1-propanesulfonate, and an oligomeric form of at least one of the group consisting of diallyldimethylammonium chloride, sodium 4-styrenesulfonate, and 3-(1-Pyridinio)-1-propanesulfonate; and
      iii) an extractant;
   b) adding said amphiphilic agent to said algae cells under conditions such that said hydrophobic cell surface is created, and
   c) purifying said algal oil with said extractant.

2. The method of claim 1 wherein said purifying releases said algal oil from said algae cells.

3. The method of claim 1 wherein said purifying uses a homogenizer to release said algal oil from said algae cells.

4. The method of claim 3 wherein said purifying releases said algal oil with said extractant.

5. The method of claim 1 wherein said algae cells are *Nannochloropsis oculata*.

6. The method of claim 1 wherein said algae cells are *Chlorella vulgaris*.

7. The method of claim 1 wherein said extractant comprises non-polar solvent.

8. A method for the extraction of protein comprising:
   a) providing:
      i) an aqueous solution comprising multi-component suspension, said multi-component suspension comprising hydrophilic protein;
      ii) an amphiphilic agent capable of converting said hydrophilic protein to a hydrophobic protein, wherein said amphiphilic agent is selected from the group consisting of: Poly(diallyldimethylammonium chloride), Poly(sodium 4-styrenesulfonate), Poly(3-(1-Pyridinio)-1-propanesulfonate), a monomeric form of at least one of the group consisting of diallyldimethylammonium chloride, sodium 4-styrenesulfonate, and 3-(1-Pyridinio)-1-propanesulfonate, and an oligomeric form of at least one of the group consisting of diallyldimethylammonium chloride, sodium 4-styrenesulfonate, and 3-(1-Pyridinio)-1-propanesulfonate; and
      iii) an extractant;
   b) adding said amphiphilic agent to said multi-component suspension, and
   c) purifying said protein with said extractant.

9. The method of claim 8 wherein said purifying releases said protein from said multi-component suspension.

10. The method of claim 8 wherein said purifying uses a homogenizer to release said protein from said multi-component suspension.

11. The method of claim 8 wherein said purifying releases said protein with said extractant.

* * * * *